(12) United States Patent
Gaddam et al.

(10) Patent No.: US 9,270,134 B2
(45) Date of Patent: Feb. 23, 2016

(54) ADAPTIVE RATE RECHARGING SYSTEM

(71) Applicant: Medtronic, Inc., Minneapolis, MN (US)

(72) Inventors: Venkat R. Gaddam, Maple Grove, MN (US); Reid K. Bornhoft, Lino Lakes, MN (US); Kevin J. Kelly, Shoreview, MN (US); David P. Olson, Minnetrista, MN (US); Todd V. Smith, Shoreview, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 405 days.

(21) Appl. No.: 13/749,481

(22) Filed: Jan. 24, 2013

(65) Prior Publication Data

US 2013/0193914 A1    Aug. 1, 2013

Related U.S. Application Data

(60) Provisional application No. 61/591,716, filed on Jan. 27, 2012.

(51) Int. Cl.
*H02J 7/00*     (2006.01)
*A61N 1/378*    (2006.01)
*H02J 7/02*     (2006.01)

(52) U.S. Cl.
CPC .............. *H02J 7/007* (2013.01); *A61N 1/3787* (2013.01); *H02J 7/0093* (2013.01); *H02J 7/025* (2013.01)

(58) Field of Classification Search
CPC ......... H02J 7/007; H02J 7/025; H02J 7/0093; A61N 1/3787
See application file for complete search history.

(56) References Cited

U.S. PATENT DOCUMENTS

| 5,702,431 | A | * | 12/1997 | Wang et al. ................... 607/61 |
| 6,099,494 | A | * | 8/2000 | Henniges et al. .............. 604/35 |
| 6,185,456 | B1 | * | 2/2001 | Garrett ........................... 607/5 |
| 6,227,204 | B1 | | 5/2001 | Baumann et al. |
| 6,313,612 | B1 | * | 11/2001 | Honda et al. ................. 320/139 |
| 6,664,763 | B2 | | 12/2003 | Echarri et al. |
| 6,878,481 | B2 | * | 4/2005 | Bushong et al. .............. 429/54 |
| 7,093,601 | B2 | | 8/2006 | Manker et al. |
| 7,339,353 | B1 | * | 3/2008 | Masias et al. ................. 320/138 |
| 7,582,387 | B2 | | 9/2009 | Howard et al. |
| 7,635,541 | B2 | | 12/2009 | Scott et al. |
| 7,734,353 | B2 | | 6/2010 | Gerber et al. |
| 7,819,826 | B2 | | 10/2010 | Diederich et al. |

(Continued)

OTHER PUBLICATIONS

Final Office Action from U.S. Appl. No. 13/360,443, dated Jul. 7, 2014, 21 pp.

(Continued)

*Primary Examiner* — Naum B Levin
(74) *Attorney, Agent, or Firm* — Shumaker & Sieffert, P.A.

(57) ABSTRACT

Devices, systems, and techniques for selecting a period for charging an implantable rechargeable power source are disclosed. Implantable medical devices may include a rechargeable power source that can be transcutaneously charged. A system may control a charging module to begin charging the rechargeable power source of the implantable medical device with a high power level. The system may then determine an estimated heat loss based on power initially delivered to the rechargeable power source when beginning the charging. Based on this estimated heat loss during the initial period of recharging, the system may select a boost period that includes a duration of time that the rechargeable power source is charged with the high power level.

33 Claims, 13 Drawing Sheets

(56) References Cited

U.S. PATENT DOCUMENTS

| | | | |
|---|---|---|---|
| 7,907,901 B1 | 3/2011 | Kahn et al. | |
| 8,134,256 B2* | 3/2012 | Onishi et al. | 307/104 |
| 8,169,185 B2* | 5/2012 | Partovi et al. | 320/108 |
| 8,278,871 B2* | 10/2012 | Kallmyer | 320/108 |
| 8,482,250 B2* | 7/2013 | Soar | 320/109 |
| 8,509,912 B2* | 8/2013 | Morgan et al. | 607/61 |
| 8,620,484 B2* | 12/2013 | Baarman et al. | 700/291 |
| 2004/0234865 A1* | 11/2004 | Sato et al. | 429/322 |
| 2007/0188323 A1 | 8/2007 | Sinclair et al. | |
| 2007/0270921 A1* | 11/2007 | Strother et al. | 607/60 |
| 2008/0019514 A1 | 1/2008 | Stromberg et al. | |
| 2008/0183165 A1 | 7/2008 | Buysse et al. | |
| 2009/0005770 A1 | 1/2009 | Gerber et al. | |
| 2009/0088623 A1 | 4/2009 | Vortman et al. | |
| 2009/0112291 A1 | 4/2009 | Wahlstrand et al. | |
| 2009/0276014 A1 | 11/2009 | Morgan et al. | |
| 2010/0010582 A1 | 1/2010 | Carbunaru et al. | |
| 2010/0047671 A1* | 2/2010 | Chiang et al. | 429/50 |
| 2010/0137948 A1* | 6/2010 | Aghassian et al. | 607/61 |
| 2010/0199092 A1 | 8/2010 | Andrus et al. | |
| 2010/0256709 A1 | 10/2010 | Kallmyer | |
| 2010/0301803 A1* | 12/2010 | Flemming | 320/110 |
| 2010/0305662 A1 | 12/2010 | Ozawa et al. | |
| 2011/0071597 A1 | 3/2011 | Aghassian | |
| 2011/0087307 A1 | 4/2011 | Carbunaru et al. | |
| 2012/0262108 A1 | 10/2012 | Olson et al. | |
| 2013/0197613 A1* | 8/2013 | Kelly et al. | 607/96 |

OTHER PUBLICATIONS

Office Action for U.S. Appl. No. 13/360,443, dated Nov. 22, 2013, 16 pages.
Response to Final Office Action mailed Jul. 7, 2014, from U.S. Appl. No. 13/360,443, filed Sep. 8, 2014, 14 pp.
International Search Report and Written Opinion from International Application No. PCT/US2013/023052, dated Sep. 23, 2013, 13 pages.
U.S. Appl. No. 13/360,443, by Kevin J. Kelly, filed Jan. 27, 2012.
U.S. Appl. No. 13/360,520, by Reid K. Bornhoft, filed Jan. 27, 2012.
U.S. Appl. No. 13/360,531, by Reid K. Bornhoft, filed Jan. 27, 2012.
U.S. Appl. No. 12/699,830, by David A. Dinsmoor, filed Feb. 3, 2010.
Office Action from U.S. Appl. No. 13/360,443, dated Jan. 16, 2015, 22 pp.
International Search Report and Written Opinion from Counterpart International Patent Application No. PCT/US2014/055544, mailed Jan. 23, 2015, 9 pp.
Response to Office Action dated Jan. 16, 2015, from U.S. Appl. No. 13/360,443, filed Jun. 16, 2015, 14 pp.
Response to Office Action dated Nov. 22, 2013, from U.S. Appl. No. 13/360,443, filed Feb. 24, 2014, 14 pages.
Final Office Action from U.S. Appl. No. 13/360,443, dated Oct. 29, 2015, 28 pages.

* cited by examiner

| HEAT LOSS (WATTS) | CHARGING CURRENT (mA) | CHARGE RATE (C) | BOOST PERIOD (SECONDS) |
|---|---|---|---|
| 1.0 | 83.6 | 1.0 | 1820 |
| 1.1 | 90.0 | 1.1 | 1530 |
| 1.2 | 96.4 | 1.1 | 1300 |
| 1.3 | 102.8 | 1.2 | 1120 |
| 1.4 | 109.2 | 1.3 | 940 |
| 1.5 | 115.6 | 1.4 | 850 |
| 1.6 | 122.0 | 1.4 | 720 |
| 1.7 | 128.4 | 1.5 | 650 |
| 1.8 | 134.8 | 1.6 | 570 |
| 1.9 | 141.2 | 1.7 | 500 |
| 2.0 | 147.6 | 1.7 | 450 |

FIG. 8A

| HEAT LOSS (WATTS) | CHARGING CURRENT (mA) | CHARGE RATE (C) | BOOST PERIOD (SECONDS) |
|---|---|---|---|
| 2.8 | 200 | 2.4 | 216 |
| 3.6 | 250 | 2.9 | 125 |
| 4.4 | 300 | 3.5 | 80 |
| 5.2 | 350 | 4.1 | 55 |
| 5.9 | 400 | 4.7 | 39 |
| 6.7 | 450 | 5.3 | 29 |
| 7.5 | 500 | 5.9 | 23 |
| 8.3 | 550 | 6.5 | 18 |
| 9.1 | 600 | 7.1 | 14 |
| 9.9 | 650 | 7.6 | 12 |
| 10.6 | 700 | 8.2 | 10 |
| 11.4 | 750 | 8.8 | 8 |
| 12.2 | 800 | 9.4 | 7 |
| 13.0 | 850 | 10.0 | 6 |

FIG. 8B

ADAPTIVE RATE RECHARGING SYSTEM

This application claims the benefit of U.S. Provisional Application No. 61/591,716, filed Jan. 27, 2012, the entire content of each of which is incorporated herein by reference.

TECHNICAL FIELD

The disclosure relates to implantable medical devices and, more particularly, rechargeable power supplies for implantable medical devices.

BACKGROUND

Implantable medical devices may be used to monitor a patient condition and/or deliver therapy to the patient. In long term or chronic uses, implantable medical devices may include a rechargeable power source (e.g., comprising one or more capacitors or batteries) that extends the operational life of the medical device to weeks, months, or even years over a non-rechargeable device.

When the energy stored in the rechargeable power source has been depleted, the patient may use an external charging device to recharge the power source. Since the rechargeable power source is implanted in the patient and the charging device is external of the patient, this charging process may be referred to as transcutaneous charging. In some examples, transcutaneous charging may be performed via inductive coupling between a primary coil in the charging device and a secondary coil in the implantable medical device.

When a current is applied to the primary coil and the primary coil is aligned to the secondary coil, electrical current is induced in the secondary coil within the patient. This induced electrical current is used to recharge the battery in the implantable medical device. Therefore, the external charging device does not need to physically connect with the rechargeable power source for charging to occur.

SUMMARY

In general, the disclosure is directed to devices, systems, and techniques for selecting a period, power level, and/or charge rate for charging an implantable rechargeable power source. An external charging device may be used to transcutaneously charge a rechargeable power source of the implantable medical device (IMD). A system may control a charging module to begin charging the rechargeable power source of the IMD with a high power level to reduce the amount of time needed for charging. However, higher heat loss from the IMD during charging may reduce the duration of charging with the high power level, e.g., to avoid an undesirable level of tissue heating. The system may thus determine an estimated heat loss based on power initially delivered to the rechargeable power source when beginning the charging. Based on this estimated heat loss during the initial period of recharging, the system may be adaptive to charging conditions and select a boost period for which the system will recharge the power source with the high power level. The high power level (e.g., a power level at hardware limits or other elevated power level over a different power level used to charge the IMD) may be a power level higher than a lower power level (e.g., a low power level used to provide a trickle charge or other charge that may not increase IMD temperatures to undesirable levels). In one example, the boost period may be selected from a stored lookup table or otherwise calculated.

In one aspect, the disclosure is directed to a method that includes controlling a charging module to begin charging a rechargeable power source of an implantable medical device with a high power level, wherein the high power level is higher than a non-zero low power level, determining, by a processor, an estimated heat loss based on power initially delivered to the rechargeable power source when beginning the charging with the high power level, selecting, by the processor, a boost period based on the estimated heat loss, and continuing to control the charging module to charge the rechargeable power source with the high power level for a duration of the boost period.

In another aspect, the disclosure is directed to a system that includes a processor configured to control a charging module to begin charging a rechargeable power source of an implantable medical device with a high power level, wherein the high power level is higher than a non-zero low power level, determine an estimated heat loss based on power initially delivered to the rechargeable power source when beginning to charge the rechargeable power source with the high power level, select a boost period based on the estimated heat loss, and continue to control the charging module to charge the rechargeable power source with the high power level for a duration of the boost period.

In a further aspect, the disclosure is directed to a computer-readable storage medium comprising instructions that cause at least one processor to control a charging module to begin charging a rechargeable power source of an implantable medical device with a high power level, wherein the high power level is higher than a non-zero low power level, determine an estimated heat loss based on power initially delivered to the rechargeable power source when beginning the charging with the high power level, select a boost period based on the estimated heat loss, and continue to control the charging module to charge the rechargeable power source with the high power level for a duration of the boost period.

In another aspect, the disclosure is directed to a system that includes means for controlling a charging module to begin charging a rechargeable power source of an implantable medical device with a high power level, wherein the high power level is higher than a non-zero low power level, means for determining an estimated heat loss based on power initially delivered to the rechargeable power source when beginning the charging with the high power level, and means for selecting a boost period based on the estimated heat loss, wherein the means for controlling the charging module to begin charging the rechargeable power source comprises means for continuing to control the charging module to charge the rechargeable power source with the high power level for a duration of the boost period.

The details of one or more example are set forth in the accompanying drawings and the description below. Other features, objects, and advantages will be apparent from the description and drawings, and from the claims.

BRIEF DESCRIPTION OF DRAWINGS

FIGS. 8A and 8B are example lookup tables with boost periods corresponding to different estimated heat loss values.

DETAILED DESCRIPTION

Figure 1:
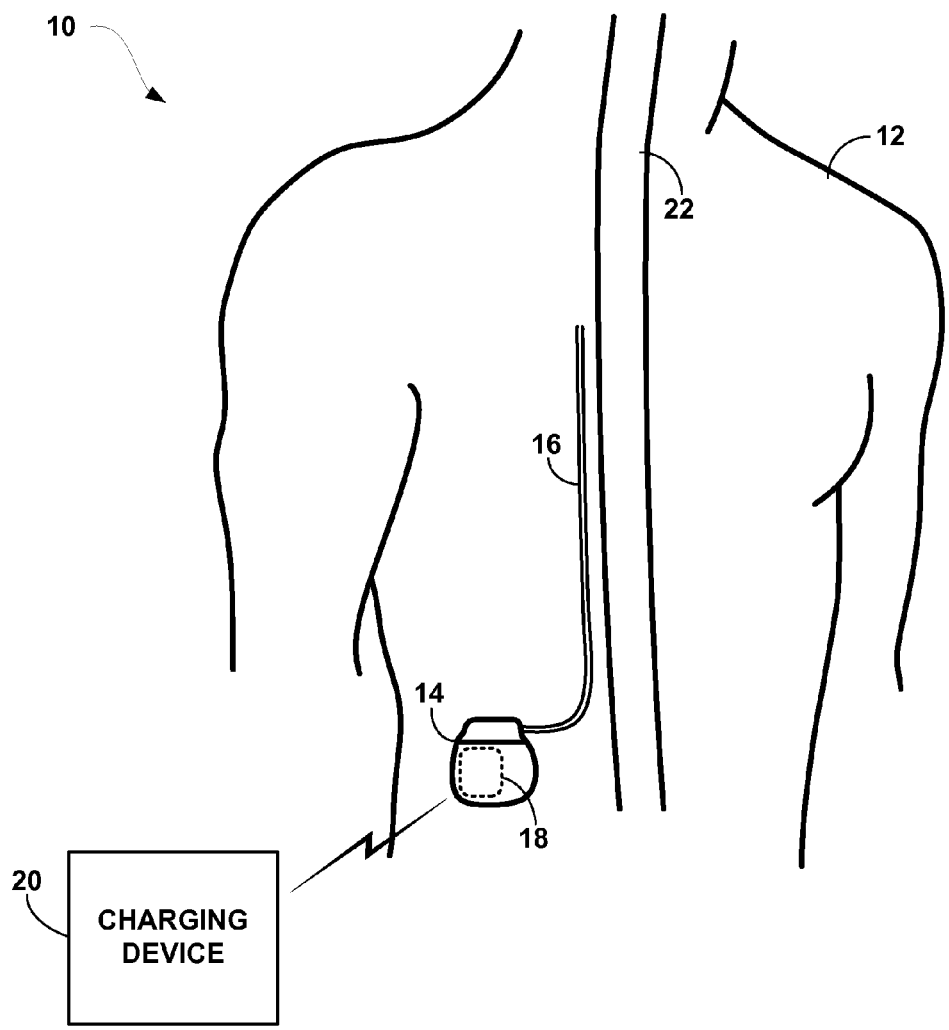
FIG. 1 is a conceptual diagram illustrating an example system that includes an implantable medical device (IMD) and an external charging device that charges a rechargeable power source of the IMD.

This disclosure is generally directed to devices, systems, and techniques for selecting a period (e.g., a boost period of a high power level) for charging an implantable rechargeable power source. Implantable medical devices (IMDs) may be implanted within a patient and used to monitor a parameter of the patient and/or deliver a therapy to the patient. To extend the operational life of the IMD, the IMD may include a rechargeable power source (e.g., one or more capacitors or batteries). When the rechargeable power source is being recharged, the power transmitted to the IMD may generate heat that increases the temperature of the IMD. As the power level of charging is increased to increase the charging rate, the temperature of the IMD increases further. In some cases, increased IMD temperatures due to faster recharging rates have the potential to cause discomfort or damage to tissue adjacent and/or surrounding the IMD. In order to reduce the potential of increased IMD temperatures damaging patient tissue adjacent to the IMD, charging sessions may be limited in duration to predetermined durations and/or reduced power levels may be used to recharge the rechargeable power source. However, this approach may increase recharge durations and/or prevent the rechargeable power source from being fully charged.

As disclosed herein, an estimated heat loss from the IMD during recharging may be determined to select a boost period for charging the rechargeable power source at a high rate without submitting the patient to potentially dangerous IMD temperatures. The boost period may be an initial period of charging with a high power level. In other words, the boost period may be a period of fast charging that reduces the overall time needed to fully recharge the rechargeable power source. The high power level of the boost period may be relatively higher than a low power level (e.g., a non-zero power level) that could be used for charging the IMD. The low power level may be used to provide a trickle charge or an average power level that may be used in non-boost charging situations. The high power level may be defined by one or more of a higher current, voltage, frequency, or pulse width than that of the low power level.

In addition, the high power level may be varied to reach a target current to the rechargeable power source. For example, the power level during the boost period may be set to a maximum limit of the charging device when the current to the rechargeable power source has not reached the targeted value. In another example, the power level of the charging device may be set below the limit of the charging device if the current delivered to the rechargeable power source reaches the target current value. The boost period may also be based on the estimated heat loss from the IMD to provide a long boost period without increasing the IMD temperature to a level that may damage surrounding tissue. In other words, longer boost periods may be selected when less heat is lost from the IMD (e.g., less heat is transmitted to tissues of the patient). The high power level of the boost period may, in some examples, be limited by hardware limitations of the charging device and/or a target value of the current delivered to the rechargeable power source.

The system may estimate the IMD heat loss during an initial period, or beginning, of the charging session. In other words, the boost period may be selected based on the heat loss estimated with measurements and/or calculations taken relatively quickly after charging is started. The heat loss estimation may be performed because the energy transfer to the rechargeable power source may vary between patients or even between charging sessions of the same patient. The initial heat loss may then be used to select a boost period appropriate for that particular charging session. In this manner, the system may be able to provide a boost period tailored to the conditions of the specific charging session without continuing to monitor the charging session. This approach of selecting a boost period based on the initial heat loss estimation may not be a fully closed-loop system in some examples.

The system (e.g., a processor of an external charging device and/or a processor of the IMD) may determine the estimated heat loss based on one or more measured parameters. For example, the system may estimate the heat loss by calculating the power delivered to a primary coil of an external charging device, calculating an amount of power lost in the primary coil, and then subtracting the amount of power lost in the primary coil and the power delivered to the rechargeable power source from the power delivered to the primary coil. These calculations may include measurements of electrical current and voltage between various components of the charging system.

Using the estimated heat loss, the system may select the appropriate boost period that has a duration of time for charging the rechargeable power source with the high power level. The boost period may be selected from multiple boost periods contained in a lookup table, for example, that each corresponds to a different estimated heat loss. The system may thus charge the rechargeable power source of the IMD with the high power level until the selected boost period expires. After the boost period expires, charging may continue at one or more lower power levels until the power source is fully charged, a cumulative thermal dose delivered to the patient exceeds a threshold, or the patient terminates charging. As discussed further below, the cumulative thermal dose may be a metric used to quantify or estimate the total temperature exposure to tissue adjacent to IMD 14. In some examples, the external charging device may notify the patient of the current power level, when the boost period is occurring, or other such information related to charging the rechargeable power source of the IMD.

In other examples, the system may select the power level and an appropriate boost period to increase the charge level of the rechargeable power source during an available time period for charging to occur. The system may provide two or more test charges before starting the boost period. During each test charge, the system may select a power level and determine the estimated heat loss during the test charge. The system may then select the appropriate boost period for each test charge based on the estimated heat loss. Based on a calculation of the forecast charge levels of the rechargeable power source using each of the tested power levels and respective boost periods, the system may select the power level and boost period that would provide the highest charge level to the rechargeable power source. In this manner, the system may select lower power levels and longer boost periods to achieve higher charge levels when a patient has a longer period of time to charge the rechargeable power source.

FIG. 1 is a conceptual diagram illustrating an example system 10 that includes an implantable medical device (IMD) 14 and an external charging device 20 that charges a rechargeable power source 18. Although the techniques described in this disclosure are generally applicable to a variety of medical devices including medical devices such as patient monitors, electrical stimulators, or drug delivery devices, application of such techniques to implantable neurostimualtors will be described for purposes of illustration. More particularly, the disclosure will refer to an implantable neurostimulation system for use in spinal cord stimulation therapy, but without limitation as to other types of medical devices.

As shown in FIG. 1, system 10 includes an IMD 14 and external charging device 20 shown in conjunction with a patient 12, who is ordinarily a human patient. In the example of FIG. 1, IMD 14 is an implantable electrical stimulator that delivers neurostimulation therapy to patient 12, e.g., for relief of chronic pain or other symptoms. Generally IMD 14 may be a chronic electrical stimulator that remains implanted within patient 12 for weeks, months, or even years. In the example of FIG. 1, IMD 14 and lead 16 may be directed to delivering spinal cord stimulation therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or other internal location. IMD 14 includes rechargeable power source 18 and IMD 14 is coupled to lead 16.

Electrical stimulation energy, which may be constant current or constant voltage based pulses, for example, is delivered from IMD 14 to one or more targeted locations within patient 12 via one or more electrodes (not shown) of lead 16. The parameters for a program that controls delivery of stimulation energy by IMD 14 may include information identifying which electrodes have been selected for delivery of stimulation according to a stimulation program, the polarities of the selected electrodes, i.e., the electrode configuration for the program, and voltage or current amplitude, pulse rate, pulse shape, and pulse width of stimulation delivered by the electrodes. Electrical stimulation may be delivered in the form of stimulation pulses or continuous waveforms, for example.

In the example of FIG. 1, lead 16 is disposed within patient 12, e.g., implanted within patient 12. Lead 16 tunnels through tissue of patient 12 from along spinal cord 22 to a subcutaneous tissue pocket or other internal location where IMD 14 is disposed. Although lead 16 may be a single lead, lead 16 may include a lead extension or other segments that may aid in implantation or positioning of lead 16. In addition, a proximal end of lead 16 may include a connector (not shown) that electrically couples to a header of IMD 14. Although only one lead 16 is shown in FIG. 1, system 10 may include two or more leads, each coupled to IMD 14 and directed to similar or different target tissue sites. For example, multiple leads may be disposed along spinal cord 22 or leads may be directed to spinal cord 22 and/or other locations within patient 12.

Lead 16 may carry one or more electrodes that are placed adjacent to the target tissue, e.g., spinal cord 22 for spinal cord stimulation (SCS) therapy. One or more electrodes may be disposed at a distal tip of lead 16 and/or at other positions at intermediate points along lead 16, for example. Electrodes of lead 16 transfer electrical stimulation generated by an electrical stimulation generator in IMD 14 to tissue of patient 12. The electrodes may be electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for therapy. In general, ring electrodes arranged at different axial positions at the distal ends of lead 16 and will be described for purposes of illustration.

In alternative examples, lead 16 may be configured to deliver stimulation energy generated by IMD 14 to stimulate one or more sacral nerves of patient 12, e.g., sacral nerve stimulation (SNS). SNS may be used to treat patients suffering from any number of pelvic floor disorders such as pain, urinary incontinence, fecal incontinence, sexual dysfunction, or other disorders treatable by targeting one or more sacral nerves. Lead 16 and IMD 14 may also be configured to provide other types of electrical stimulation or drug therapy (e.g., with lead 16 configured as a catheter). For example, lead 16 may be configured to provide deep brain stimulation (DBS), peripheral nerve stimulation (PNS), or other deep tissue or superficial types of electrical stimulation. In other examples, lead 16 may provide one or more sensors configured to allow IMD 14 to monitor one or more parameters of patient 12. The one or more sensors may be provided in addition to, or in place of, therapy delivery by lead 16.

IMD 14 delivers electrical stimulation therapy to patient 12 via selected combinations of electrodes carried by lead 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 16 is tissue proximate spinal cord 22 (e.g., one or more target locations of the dorsal columns or one or more dorsal roots that branch form spinal cord 22. Lead 16 may be introduced into spinal cord 22 via any suitable region, such as the thoracic, cervical or lumbar regions. Stimulation of dorsal columns, dorsal roots, and/or peripheral nerves may, for example, prevent pain signals from traveling through spinal cord 22 and to the brain of the patient. Patient 12 may perceive the interruption of pain signals as a reduction in pain and, therefore, efficacious therapy results. For treatment of other disorders, lead 16 may be introduced at any exterior location of patient 12. In this manner, skin opening 18 may be located at any exterior skin location in other examples.

Although lead 16 is described as generally delivering or transmitting electrical stimulation signals, lead 16 may additionally or alternatively transmit electrical signals from patient 12 to IMD 14 for monitoring. For example, IMD 14 may utilize detected nerve impulses to diagnose the condition of patient 12 or adjust the delivered stimulation therapy. Lead 16 may thus transmit electrical signals to and from patient 12.

A user, such as a clinician or patient 12, may interact with a user interface of an external programmer (not shown) to program IMD 14. Programming of IMD 14 may refer generally to the generation and transfer of commands, programs, or other information to control the operation of IMD 14. For example, the external programmer may transmit programs, parameter adjustments, program selections, group selections, or other information to control the operation of IMD 14, e.g., by wireless telemetry or wired connection.

In some cases, an external programmer may be characterized as a physician or clinician programmer if it is primarily intended for use by a physician or clinician. In other cases, the external programmer may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use. In other examples, external charging device 20 may be included, or part of, an external programmer. In this manner, a user may program and charge IMD 14 using one device, or multiple devices.

IMD 14 may be constructed of any polymer, metal, or composite material sufficient to house the components of IMD 14 (e.g., components illustrated in FIG. 2) within patient 12. In this example, IMD 14 may be constructed with a biocompatible housing, such as titanium or stainless steel, or a polymeric material such as silicone or polyurethane, and surgically implanted at a site in patient 12 near the pelvis, abdomen, pectoral muscles, armpit, base of the skull, buttocks, or other locations. The housing of IMD 14 may be configured to provide a hermetic seal for components, such as rechargeable power source 18. In addition, the housing of IMD 14 may be selected of a material that facilitates receiving energy to charge rechargeable power source 18.

As described herein, rechargeable power source 18 may be included within IMD 14. However, in other examples, rechargeable power source 18 could be located external to a housing of IMD 14, separately protected from fluids of patient 12, and electrically coupled to electrical components of IMD 14. This type of configuration of IMD 14 and rechargeable power source 18 may provide implant location flexibility when anatomical space for implantable devices is minimal. In any case, rechargeable power source 18 may provide operational electrical power to one or more components of IMD 14.

Rechargeable power source 18 may include one or more capacitors, batteries, or components (e.g. chemical or electrical energy storage devices). Example batteries may include lithium-based batteries, nickel metal-hydride batteries, or other materials. Rechargeable power source 18 is also rechargeable or replenishable. In other words, rechargeable power source 18 may be replenished, refilled, or otherwise capable of increasing the amount of energy stored after energy has been depleted. Rechargeable power source 18 may be subjected to numerous discharge and recharge cycles (e.g., hundreds or even thousands of cycles) over the life of rechargeable power source 18 in IMD 14. Rechargeable power source 18 may be recharged when fully depleted or partially depleted.

For example, rechargeable power source 18 may be a lithium-ion battery that is configured to be charged at relatively high charging rates and/or configured to be discharged to a very low voltage (e.g., approximately zero volts) without causing permanent damage to the battery. In one example, such a rechargeable battery may be constructed using a titanium-based material as at least part of the negative active material of the negative electrode (e.g., an anode) of the battery. In this manner, rechargeable power source 18 may include one or more negative electrodes that each include lithium titanate. The titanium-based material may include pure titanium or a titanium alloy. For example, the titanium alloy may be a lithium titanate material, such as $Li_4Ti_5O_{12}$, that is used as part of the negative active material of the negative electrode. Hence, the negative electrode may comprise lithium titanate. The lithium titanate material may be used in place of a negative active material containing copper or a carbonaceous material such as graphite to facilitate higher charge rates and/or protect against low voltage damage to the battery. Other example negative active materials may include nickel, nickel alloys, and stainless steel. A positive active material of the positive electrode may include, for example, lithium and cobalt and/or nickel. In one example, the positive active material may include lithium cobalt oxide.

Lithium titanate materials, as an example of titanium-based negative active materials, may allow rechargeable power source 18 to achieve desirable charging characteristics. In one example, rechargeable power source 18 may be configured to achieve high charge rates up to or greater than 10 C (i.e., attaining full charge in ⅒ hours, or six minutes). The charge rate of rechargeable power source 18 may be limited by the current that IMD 14 is capable of producing during a recharge session. In another example, rechargeable power source 18 may be fully discharged to a very low voltage of approximately zero volts. After rechargeable power source 18 reaches this fully discharged voltage, rechargeable power source 18 may again be charged without any performance degradation to the battery that may otherwise occur without the lithium titanate material. Moreover, the high charge rate of rechargeable power source 18 may be achieved immediately upon recharging a fully discharged, or depleted, power source 18. In addition, lithium titanate materials used as a negative active material of rechargeable power source 18 may allow rechargeable power source 18 to be charged in a constant voltage mode in other words, IMD 14 may apply a voltage source across rechargeable power source 18 such that electrical charging current enters rechargeable power source 18 as fast as the charging circuitry and battery chemistry allows.

Charging device 20 may be used to recharge rechargeable power source 18 and IMD 14 when implanted in patient 12. Charging device 20 may be a hand-held device, a portable device, or a stationary charging system external to patient 12. In any case, charging device 20 may include components necessary to charge rechargeable power source 18 through tissue of patient 12. In some examples, charging device 20 may only perform charging of rechargeable power source 18. In other examples, charging device 20 may be an external programmer or other device configured to perform additional functions. For example, when embodied as an external programmer, charging device 20 may transmit programming commands to IMD 14 in addition to charge rechargeable power source 18. In another example, charging device 20 may communicate with IMD 14 to transmit and/or receive information related to the charging of rechargeable power source 18. For example, IMD 14 may transmit temperature information of IMD 14 and/or rechargeable power source 18, received power during charging, the charge level of rechargeable power source 18, charge depletion rates during use, or any other information related to power consumption and recharging of IMD 14 and rechargeable power source 18.

Charging device 20 and IMD 14 may utilize any wireless power transfer techniques that are capable of recharging rechargeable power source 18 of IMD 14 when IMD 14 is implanted within patient 14. In one example, system 10 may utilize inductive coupling between a coil of charging device 20 and a coil of IMD 14 coupled to rechargeable power source 18. In inductive coupling, charging device 20 is placed near implanted IMD 14 such that a primary coil of charging device 20 is aligned with, i.e., placed over, a secondary coil of IMD 14. Charging device 20 may then generate an electrical current in the primary coil based on a selected power level for charging rechargeable power source 18. As described further below, the power level may be selected to control or limit the temperature of IMD 14 and/or the charge rate of rechargeable power source 18. When the primary and secondary coils are aligned, the electrical current in the primary coil may magnetically induce an electrical current in the secondary coil within IMD 14. Since the secondary coil is associated with and electrically coupled to rechargeable power source 18, the induced electrical current may be used to increase the voltage, or charge level, of rechargeable power source 18. Although inductive coupling is generally described herein, any type of wireless energy transfer may be used to charge rechargeable power source 18.

During the energy transfer process that charges rechargeable power source 18, some of the energy may be converted into heat at rechargeable power source 18 and/or other components of IMD 14. This heat may be referred to as heat loss within IMD 14 during charging. In other words, heat loss may be energy transformed into heat or electrical current dissipated in the resistive loading presented by the coil in the form of heat instead of transformed into electrical current that charges rechargeable power source 18. When increased energy levels (e.g., higher power level) are used to charge rechargeable power source 18 at a higher rate, the temperature of IMD 14 may also increase. Although the temperature of the housing of IMD 14 may not achieve a temperature sufficient to burn or necrose tissue adjacent to the housing of IMD 14, elevated temperatures may be undesirable and uncomfortable over time. Therefore, charging device 20 may control the power levels and or duration a power level is used to charge rechargeable power source 18 to reduce or minimize any undesirable temperatures of IMD 14 that could be caused by charging rechargeable power source 18. In some examples, monitoring the temperature of IMD 14 and/or the temperature of tissue adjacent to the housing of IMD 14 may also minimize patient discomfort during the charging process.

This disclosure generally describes the heat induced in IMD 14 during the charging process as the estimated heat loss (e.g., the charging energy from charging device 20 converted to heat in IMD 14 instead of charging current in IMD 14). Since some or all of this IMD heat may be transferred to adjacent tissues of the patient, this estimated heat loss may be used to determine the duration of a boost period. However, this estimated heat loss during charging may alternatively be described has an estimated heat generated or heat induced within IMD 14. In other words, an estimated heat loss and an estimated heat generated may represent the same heating condition in IMD 14 during charging. The duration of the boost period may thus be described as being selected based on either the estimated heat loss or the estimated heat generated during charging. In any case, charging device 20, IMD 14, or a combination thereof, may control charging of rechargeable power source 18 based on the heat (e.g., the estimated heat loss or heat generated) in IMD 14 during the charging process.

In some examples, charging device 20 and/or IMD 14 may factor in additional heat sources when estimating the heat loss or heat generation that may increase patient tissue temperatures during charging of rechargeable power source 18. These additional heat sources may include charging device 20 (e.g., increased temperate of the primary coil or other components that increase the temperature of the housing of charging device 20 placed against the skin of patient 12) or other components within IMD 14 (e.g., processing circuitry, telemetry modules, therapy modules, or any other components that may increase the temperature of IMD 14), for example. The heat from these additional heat sources may be estimated by detecting or calculating electrical currents within the respective sources and/or sensing temperature via one or more temperature sensors. In this manner, charging device 20 or IMD 14 may be configured to select a boost period based on an estimated heat loss or heat generated within IMD 14 or the entire system 10 (e.g., charging device 20 and IMD 14) based on several factors that may or may not be directly caused by the charging process.

In one example, charging device 20, IMD 14, or a combination thereof, may estimate a heat loss from rechargeable power source 18 and select a boost period for charging with a high power level according to the estimated heat loss. In this manner, the boost period may be selected to increase the amount of time for fast charging of rechargeable power source 18 while limiting potential of elevated IMD temperatures that may damage adjacent tissue. A processor of charging device 20 may initially control a charging module (e.g., a charging module of charging device 20) to begin charging rechargeable power source 18 of IMD 14 with a high power level. A processor (e.g., a processor of charging device 20 or IMD 14) may then determine an estimated heat loss based on power initially delivered to rechargeable power source 18 when the charging module begins the charging. The processor may then select a boost period based on the estimated heat loss for the remainder of the charging session. As described herein, the boost period may define the duration of time that rechargeable power source 18 is charged with the high power level.

The high power level may be relatively higher than a low power level that may be used to charge rechargeable power source 18. Both the high power level and the low power level may be a non-zero power level. The high power level may also be defined by one or more parameters, e.g., a voltage, a current, and a frequency. The high power level may have one or more of a higher voltage, a higher current, and a higher frequency than that of a low power level. The low power level may be a power level used in a non-boost condition or a trickle charge condition. Generally, the high power level may increase the temperature of IMD 14 at a higher rate than a low power level when charging coils are similarly aligned. The high power level may generally be constant during the boost period. However, the high power level may fluctuate slightly due to operational variations even when the system is set to a constant power level.

One or more components of system 10 (e.g., a processor of charging device 20) may estimate the heat loss from IMD 14 at some point in time during charging rechargeable power source 18. For example, charging device 20 may estimate the heat loss during the beginning of charging or within an initial period of charging. The heat loss may thus be estimated immediately after beginning the charging (e.g., as fast as measurements can be made and heat loss can be calculated by charging device 20) or within a predetermined time period. The predetermined time period may be between approximately 0.5 seconds and 30 seconds from the start of the charging session. In any example, it may be desirable to estimate the heat loss quickly after starting to charge rechargeable power source 18 in order for the selected boost period to provide accurate heat losses to patient 12. In other words, charging prior to starting the boost period may heat surrounding tissue beyond desired limits. The selected boost period may not account for the additional heat losses from charging prior to starting the boost period.

System 10 may determine the estimated heat loss by measuring one or more parameters of the charging session. For example, system 10 may calculate the power initially delivered to rechargeable power source 18 when starting the charging session. Calculating the power delivered to rechargeable power source 18 may include measuring an electrical current flowing to rechargeable power source 18, measuring a voltage of rechargeable power source 18, and multiplying the measured electrical current by the measured voltage. One or more processors may be configured to perform these calculations. A charging module or other circuit may be configured to perform the measurements. The measurements may occur by one or more circuits of IMD 14. In other examples, information related to these measurements may be transmitted to charging device 20 for processing and further calculations needed to complete the measurements. The measured electrical current and voltage may be dependent on several factors, such as the power level used by charging device 20, the magnetic field generated by a primary coil of charging device 20, the alignment between the primary coil and a secondary coil associated with rechargeable power source 18, the distance between the primary and secondary coils, orientation of the secondary coil, and other hardware characteristics. In this manner, the measured parameters of the charging session (e.g., electrical current and voltage associated with rechargeable power source 18) may differ between components of system 10, between different patients, and between different charging sessions. Consequently, the heat loss estimated by system 10 may change each time it is calculated. Patient 12 may thus also benefit from customization to the boost period of a specific charging session.

In addition to the power delivered to rechargeable power source 18, system 10 may make other calculations to determine the estimated heat loss. For example, a processor of system 10 may calculate power delivered to a primary coil of external charging device 20 and calculate power lost in the primary coil during charging. System 10 may then estimate the heat loss by subtracting the power lost in the primary coil and the power delivered to rechargeable power source 18 from the power delivered to the primary coil. In some examples, other heat losses in system 10 may be included in the estimation of the heat loss. For example, system 10 may determine the power lost in one or more circuits of IMD 14 and also subtract this circuit power loss from the power delivered to the primary coil. Although perhaps not necessary for selecting a boost period, the greater number of heat losses included in the calculation may increase the accuracy of the estimating heat loss.

The power delivered to the primary coil of charging device 20 may be calculated by multiplying the electrical current delivered to the primary coil by the voltage delivered to the primary coil and the cosine of the phase angle between the current and voltage waveforms. Charging device 20 may be configured with one or more circuits (e.g., a charging module) to measure these currents and voltages. In some examples, circuitry of charging device 20 may be tuned such that the current and voltage are in phase (e.g., the phase angle is zero and the cosine of the phase angle is equal to one). The power lost in the primary coil may be calculated by multiplying the known resistance of the primary coil by the square of the electrical current of the primary coil. In addition, the power lost in circuitry of IMD 14 may be either calculated based on one or more voltage and/or current measurements or predetermined and stored in a memory based on known design aspects of IMD 14. These calculations are merely exemplary, and other calculations using measured or known electrical parameters may be used to determine various power values within system 10.

Once the estimated heat loss is determined, system 10 may select the appropriate boost period for charging rechargeable power source 18 with the high power level. The appropriate boost period may be a boost period that allows the high power level charging rate (e.g., a fast charging rate) to continue for as long as possible before the tissue adjacent IMD 14 is exposed to undesired amounts of heat (e.g., temperature). In one example, a processor of charging device 20 or IMD 14 may select the boost period from one of a plurality of boost periods that corresponds to the estimated heat loss. The plurality of boost periods may be stored in a lookup table and each includes a different duration of time. In other words, each of the boost periods may be associated with a specific heat loss value or a range of heat loss values, which serve as index values into the lookup table to select corresponding boost periods. The lookup table of boost periods may be stored in a memory of charging device 20 and/or IMD 14. In other examples, the boost period may be calculated with one or more equations using the estimated heat loss.

The duration of time for each boost period may be determined using one or more heating models that account for tissue heating from IMD 14. In other words, the various boost periods in a lookup table may be provided from example heat losses and heating models for tissue of patient 12. Alternatively, the boost period may be calculated directly by inputting the estimated heat loss into the one or more tissue heating models. The different boost periods may be associated to the quality of coupling between the primary and secondary coils of system 10. More efficient coupling (e.g., better alignment) may lead to less heat loss and longer boost periods when the high power level may be varied to achieve a target current delivered to rechargeable power source 18. Conversely, less efficient coupling between the coils may lead to more heat loss and shorter boost periods when the high power level may be increased to achieve the target current delivered to rechargeable power source 18. Generally, the boost period may have a duration between approximately 5 minutes and approximately 35 minutes. In one example, the boost period may have a duration between approximately 10 minutes and approximately 25 minutes. Alternatively, the boost period may be selected to be less than 5 minutes or greater than 35 minutes. The boost period is at least partially dependent upon the power level used to recharge rechargeable power source 18 during the charge session. Lower power levels may thus allow greater boost periods, and higher power levels may thus allow shorter boost periods.

As described herein, charging device 20 may charge rechargeable power source 18 with a high power level for the duration of the selected boost period. Charging rechargeable power source 18 may utilize inductive coupling or other transcutaneous charging method. With inductive coupling, charging device 20 may be configured to generate a first electrical current in the primary coil of charging device 20 based on the high power level. In some examples, the high power level may be the highest power level charging device 20 is capable of producing to minimize charge times. System 10 may also include a secondary coil associated with rechargeable power source 18 and IMD 14 and implanted within patient 12. The secondary coil may produce a second electrical current that is induced in the secondary coil by the magnetic field created by the primary coil. The second electrical current may then be used to charge rechargeable power source 18, either directly or upon conditioning of the second electrical current using appropriate charging circuitry.

During the charging session, one or more circuits (e.g., a charging module) may measure one or more electrical parameters related to the charging session. For example, IMD 14 may measure electrical current flowing to rechargeable power source 18 and a measured voltage of rechargeable power source 18. IMD 14 may then include a telemetry module (not shown in FIG. 1) that is configured to transmit charging data from IMD 14 to a telemetry module of charging device 20. The charging data may include any electrical parameters associated with charging, such as the measured electrical current and the measured voltage of the rechargeable power source.

System 10 may terminate charging of rechargeable power source 18 with the high power level when the high power charging time exceeds the selected boost period. During the boost period, charging device 20 and/or IMD 14 may compare the high power charging time to the boost period, where the high power charging time is an elapsed time with which rechargeable power source 18 was charged with the high power level. Charging device 20 may stop the charging session completely upon expiration of the boost period and/or rechargeable power source 18 is fully charged.

Alternatively, charging device 20 may switch to a lower power level (e.g., a slower charging rate) and continue charging rechargeable power source 18 until rechargeable power source 18 is fully charged or the charging session is otherwise terminated or interrupted. The lower power level may transmit less energy to IMD 14 and thus reduce the heat being delivered to patient 12. In some examples, the lower power level may be selected such that the heat loss with the lower power level can continue indefinitely without damaging patient tissue. In this manner, system 10 may select a low power level when the high power charging time exceeds the boost period and continue to charge rechargeable power source 18 with the low power level until rechargeable power source 18 is fully charged. The low power level may be any power level lower than the high power level.

In other examples, system 10 may continue charging rechargeable power source 18 in a closed loop manner after the boost period expires. For example, system 10 may monitor the cumulative thermal dose delivered to patient 12 after and/or during the boost period to ensure that tissue adjacent to IMD 14 is not exposed to potentially damaging temperatures. For example, one or more components of system 10 (e.g., charging device 20 and/or IMD 14) may calculate an estimated cumulative thermal dose delivered to patient 12 during charging of rechargeable power source 18 over at least the duration of the boost period. System 10 may then select a subsequent power level for charging rechargeable power source 18 after the boost period based on the estimated cumulative thermal dose. In another example, system 10 may only monitor the cumulative thermal dose delivered to patient 12 after the boost period has expired. Example methods of calculating the estimated cumulative thermal dose are is described herein.

The power level used by charging device 20 to recharge rechargeable power source 18 after the boost period may be selected or controlled based on a cumulative thermal dose delivered to patient 12 by IMD 14. The cumulative thermal dose may be a metric used to quantify or estimate the total temperature exposure to tissue adjacent to IMD 14. As such, the cumulative thermal dose may be an estimated cumulative thermal dose. In one example, the cumulative thermal dose may be calculated by integrating the tissue temperature over a period of time. The period of time may include the boost period and/or the time of charging after the boost period. The resulting cumulative thermal dose may be used to equate the delivered heat to a certain tissue temperature level for a certain period of time. For example, the clinician may want to limit tissue exposure to heat for 30 minutes at 43 degrees Celsius. However, the temperature of IMD 14 will likely vary from any one temperature over the charging period. Calculation of the cumulative thermal dose may thus allow charging device 20, or IMD 14, to determine when the desired limit to heat exposure is reached even if the actual tissue temperature varies over time. In other examples, the cumulative thermal dose may be calculated by adding the average temperature for multiple segments of the predetermined period of time. In any example, the cumulative thermal dose may be used to determine the total amount of heat, or the amount of heat lost over a selected period of time, or the extent of elevated temperature exposure for tissue surrounding and/or adjacent to IMD 14.

The tissue temperature used to calculate the cumulative thermal dose may be determined using several different techniques. Each technique may result in a cumulative thermal dose that estimates the actual cumulative thermal dose received by patient 12. However, the estimated cumulative thermal dose calculated by system 10 may be substantially similar to the actual cumulative thermal dose received by patient 12. In one example, the tissue temperature may be measured at one or more locations of IMD 14. IMD 14 may include one or more thermocouples, thermistors, or other temperature sensing elements near the inner surface of the housing of IMD 14, built within the housing, or disposed on the external of IMD 14. In other examples, IMD 14 may include one or more temperature sensing elements that extend from the outer surface of IMD 14. This direct tissue temperature measurement may be the most accurate. However, the tissue temperature measurements may need to be transmitted to charging device 20 such that a processor of charging device 20 can calculate the cumulative thermal dose. Alternatively, a processor of IMD 14 may use the measured tissue temperature to calculate the cumulative thermal dose. The processor of IMD 14 may then transmit the cumulative thermal dose such that charging device 20 can select the power level, or the processor of IMD 14 may directly select the power level based on the cumulative thermal dose and instruct charging device 20 on the power level to be used for charging.

In another example, the tissue temperature may be indirectly calculated, or estimated, based on a tissue model and the power transmitted to rechargeable power source 18 over a period of time. Charging device 20 may monitor the generated current in the primary coil and the resulting power transmitted from charging device 20 to the secondary coil located in IMD 14. The transmitted power may be calculated using the generated electrical current, estimated based on the generated electrical current and expected energy losses due to heat and misalignment, estimated based on the generated electrical current and energy losses due to misalignment, or some combination therein. In this manner, charging device 20 may unilaterally determine the tissue temperature. Alternatively, IMD 14 may measure the actual electrical current induced in the secondary coil coupled to rechargeable power source 18. Based on this measured current, a processor of IMD 14 may calculate the power transmitted from charging device 20. IMD 14 may then transmit the calculated power transmitted from charging device 20 back to charging device 20.

The measured or estimated power transmitted from charging device 20 to rechargeable power source 18 may then be applied to a tissue model to calculate the expected tissue temperature. The tissue model may be represented by one or more equations that incorporate one or more of the heat capacity of tissue adjacent IMD 14, density of surrounding tissue, inherent body temperature, surface area of the housing of IMD 14, estimated surface area of tissue surrounding IMD 14, depth of IMD 14 from the skin of patient 12, orientation of the secondary coil within patient 12, or any other variable that would affect the temperature of surrounding and/or in immediate contact with the housing of IMD 14. The tissue model may even be modified over time to account for tissue ingrowth, scar tissue, encapsulation, changes in vascularization, and other tissue changes due to the biological interaction between the housing of IMD 14 and patient 12. The transmitted power may be inputted into the tissue model to calculate an estimation of the tissue temperature as charging device 20 recharges rechargeable power source 18.

Using the transmitted power techniques, the tissue temperature may be calculated by processors of charging device 20, IMD 14, or some combination thereof. For example, charging device 20 may unilaterally calculate the tissue temperature using the tissue model and measured power transmitted to IMD 14. In another example, one or more measured variables may be communicated from IMD 14 to charging device 20 such that the charging device can calculate the tissue temperature. IMD 14 may transmit detected alignment of the primary and secondary coils and/or the electrical current induced in the secondary coil. In an alternative embodiment, IMD 14 may measure the transmitted power and calculate the tissue temperature based on that measured power transmitted from charging device 20. IMD 14 may then transmit the calculated tissue temperature to charging device 20, calculate and transmit the cumulative thermal dose to charging device 20 based on the tissue temperature, or even transmit a selected power level for charging device 20 based on the calculated cumulative thermal dose. According to these examples, the processes needed to determine a tissue temperature (e.g., using a measured temperature or tissue model calculation) and calculate the cumulative thermal dose may be performed independently by one of charging device 20 or IMD 14 or collectively through communication between charging device 20 and IMD 14.

As described herein, information may be transmitted between charging device 20 and IMD 14. Therefore, IMD 14 and charging device 20 may communicate via wireless communication using any techniques known in the art. Examples of communication techniques may include, for example, low frequency or radiofrequency (RF) telemetry, but other techniques are also contemplated. In some examples, charging device 20 may include a programming head that may be placed proximate to the patient's body near the IMD 14 implant site in order to improve the quality or security of communication between IMD 14 and charging device 20. Communication between charging device 20 may occur during or separate from power transmission.

The cumulative thermal dose is a metric that may reflect the amount of heat delivered to tissue over a period of time. Since tissue does dissipate heat, the amount of heat delivered to the tissue does not continually compound over the life of patient 12. Instead, the total amount of delivered heat may only be significant over a certain period of time. This period of time may be set by the manufacturer or the clinician to a certain number of minutes, hours, or even days. Generally, the period used to calculate the cumulative thermal dose may be between approximately 10 minutes and 10 days. More specifically, the period used to calculate the cumulative thermal dose may be between approximately one hour and 48 hours. In one example, the period may be set to approximately 24 hours. This period may be a rolling period that extends back from current time. In other words, if the period is 24 hours, the cumulative thermal dose may be the total amount of degree-minutes in the last 24 hours. In other examples, the period of time may be represented as an event. For example, the period of time may be established as a single recharge session (e.g., a continuous transmission of charging power transmitted from charging device 20 to IMD 14 that may or may not include the boost period). Therefore, the period may be defined by time or events.

The cumulative thermal dose may be utilized by system 10 to control the power transmitted from charging device 20 to IMD 14, the rate of recharging rechargeable power source 18, and the heat generated by IMD 14 during the recharging process. Accordingly, system 10, e.g., one or more processors of charging device 20 and/or IMD 14, may calculate a cumulative thermal dose delivered to patient 12 during charging of rechargeable power source 18 of IMD 14 over a period of time. The one or more processors of system 10 may then select a power level for subsequent charging of the rechargeable power source based on the calculated cumulative thermal dose. Charging device 20 may then charge rechargeable power source 18 with the selected power level. As discussed in greater detail below, the selected power level may change during the charging session to control the heat, and cumulative thermal dose, transmitted to tissue surrounding IMD 14. Although a processor of IMD 14 may select the charging power level, a processor of charging device 20 will be described herein as selecting the charging power level for purposes of illustration.

In one example, charging device 20 may select a high power level when the cumulative thermal dose has still not exceeded a thermal dose threshold after the boost period and select a low power level when the cumulative thermal dose has exceeded the thermal dose threshold. In this manner, the high power level may charge rechargeable power source 18 at a high rate to reduce charging time while increasing the temperature of IMD 14. Once the cumulative thermal dose from the elevated IMD 14 temperature exceeds the thermal dose threshold, charging device 20 may select a low power level to charge rechargeable power source 18 at a slower rate to reduce the temperature of IMD 14. The low power level may be sufficiently minimal so that any increase in temperature of IMD 14 may have minimal or no effect on surrounding tissue.

A high power level and a low power level may be subjective and relative to the charging power that charging device 20 is capable of generating and transmitting to IMD 14. In some cases, the high power level may be the maximum power that charging device 20 can generate. In other words, the high power level may only be limited by hardware limitations of charging device 20 and/or IMD 14. This high power level may be referred to as a "boost" or "accelerated" charging level because of the high rate of charge induced in rechargeable power source 18. This high rate of charge may minimize the amount of time patient 12 needs to recharge rechargeable power source 18. By monitoring the cumulative thermal dose, charging device 20 may charge rechargeable power source 18 with the high power level for a longer period of time without damaging tissue surrounding IMD 14. The high power level may even be used beyond the boost period in situations where less heat was lost during the boost period than was estimated when beginning the charging session. In other words, merely estimating the amount of time that charging device 20 can charge at the high power level without calculating the actual cumulative thermal dose may expose tissue to an undesired level of heat or underutilize the high power charging, resulting in longer total charge times. Therefore, using the cumulative thermal dose delivered to patient 12 may allow system 10 to more effectively balance fast charge times and safe heating levels.

In one example, the high power level may be approximately 2.5 Watts (W) and the low power level may be approximately 0.1 W. An example charge current level for the current in the primary coil may be approximately 100 milliamps (mA) or 120 mA for the high power level and approximately 50 mA for the low power level. The frequency of the charging signal may be independent of the power level, but the pulse width may generally increase with higher power levels assuming a constant H-bridge voltages. An H-bridge circuit may be used as one method to drive the primary coil of charging device 20 with an alternating current. An H-bridge circuit may have alternating pairs of switches (e.g., transistors) which may be gated on and off using pulses. For example, the width of such pulses may be approximately 4000 microseconds (nS) for a high power level and approximately 2000 nS for a low power level with an H-bridge voltage of approximately 10 volts (V). Each switch pair may be enabled with a respective pulse train wherein the pulses have a pulse width as specified herein. In one example, the amplitude of the voltage provided by the voltage source may be approximately 10 V. An example primary coil voltage and current for a high power may be approximately 450 V and approximately 800 mA, respectively, and an example primary coil voltage and current for a low power level may be approximately 250 V and approximately 500 mA. These values are merely examples, and other examples, may include higher or lower values in accordance with the techniques described herein.

The thermal dose threshold may be the maximum cumulative thermal dose identified as still being safe to patient 12. In other words, the thermal dose threshold may be established or selected to prevent tissue from being heated to an elevated level and duration that could be uncomfortable or undesirable. The thermal dose threshold may be preset by the manufacturer or selected by a clinician. The thermal dose threshold may also be modified over time as needed. In some examples, the thermal dose threshold may not be set to the maximum safe dose. Instead, the thermal dose threshold may be set to a lower value to establish a safety margin below the thermal dose threshold that minimizes potential overheating of tissue.

The thermal dose threshold may be based on equivalent heating of the tissue at a certain temperature for a predetermined amount of time. In other words, the thermal dose threshold may be expressed as the total degrees over time in elevated temperature. In one example, the thermal dose threshold may be selected as the equivalent to tissue at 43 degrees Celsius for 30 minutes. In another example, the thermal dose threshold may be selected as the equivalent to tissue at 43 degrees Celsius for 50 minutes. In an alternative example, the thermal dose threshold may be selected as the equivalent to tissue at 41.5 degrees Celsius for 4 hours. These thresholds may be summed for comparison to the cumulative thermal dose. For example, tissue at 43 degrees Celsius for 30 minutes may be expressed by a single value after summing or integrating the tissue temperature elevation (e.g., the difference between 43 degrees Celsius and normal body temperature of 37 degrees Celsius) over the time limit. When the cumulative thermal dose is calculated in a similar manner, the cumulative thermal dose may be compared to the thermal dose threshold as charging device 20 recharges rechargeable power source 18.

The cumulative thermal dose may be calculated by the following equation (1).

$$CEM43 = \sum_{i=1}^{N} R^{(43-T)} t_i \quad (1)$$

"CEM 43" refers to the cumulative equivalent minutes at 43 degrees Celsius for constant temperature epochs (e.g., reference data). $T_i$ is the measured temperature in degrees Celsius, and t, is the duration of time in minutes. R is a characterizing parameter, or constant, that may be set to 0.25 for temperatures less than 43 degrees Celsius. The value of R may be determined experimentally based on known cell and/or tissue characteristics, and R may be a different value in other examples. For example, a CEM 43 limit of 5 minutes may be used as cumulative thermal dose threshold and the power level may be chosen such that the cumulative thermal dose of the recharge session may remain lower than the set cumulative thermal dose threshold. In one example, the tissue temperature may be limited to 42 degrees Celsius for the entire recharge session by selecting a certain power level of charging, and the thermal dose threshold would be reached in 20 minutes (e.g., (0.25^(43-42)*20=5 minutes)). Incorporating rising and falling temperatures over time that occur when charging may be taken into effect (e.g., integrating temperature over time) to allow for longer recharge durations than would be possible by estimating a constant temperature at any particular power level.

Charging device 20 may select between two, three, or even a greater number of discrete power levels or select the power level from a continual range of available power levels. For example, charging device 20 may select between a high, medium, low, and zero (e.g., no transmitted power) power levels to minimize charging times and minimize uncomfortable or undesirable temperatures in surrounding tissue. In another example, charging device 20 may continually adjust the power level in small increments, where the increments are established by the available resolution of the current able to be generated in the primary coil of charging device 20. Therefore, these more adjustable power levels may result in a power level curve over time as opposed to individual steps in power levels that would be present using only high and low power levels. In any example, the transmitted power from charging device 20 to IMD 14 may be varied based on the calculated cumulative thermal dose.

In another example, charging device 20 may select a zero power level when the cumulative thermal dose has exceeded the thermal dose threshold. This zero power level would stop charging rechargeable power source 18 because charging device 20 would terminate current to the primary coil in response to the selection of the zero power level. Although low power levels may be used to charge rechargeable power source 18 at low rates (e.g., a trickle charge), terminating charging with the zero power level may allow IMD 14 to cool down at the fastest rate and minimize any additional heating of the tissue surrounding IMD 14. In addition, the zero power level may be selected when rechargeable power source 18 has been fully charged.

In an additional example, charging device 20 may reduce charging power levels in anticipation of meeting or exceeding the thermal dose threshold. Charging device 20 may calculate an available thermal dose by subtracting the cumulative thermal dose from the thermal dose threshold. In other words, the available thermal dose may be the thermal dose remaining before the cumulative thermal dose exceeds the thermal dose threshold. This available thermal dose may be used to reduce power levels of charging prior to exceeding the thermal dose threshold. The available thermal dose may be compared to a high power dose requirement that indicates the power should be reduced because the cumulative thermal dose is approaching the thermal dose threshold. The high power dose requirement may be set to a percentage of the thermal dose threshold, e.g., between 70 percent and 95 percent of the thermal dose threshold. The high power dose requirement may instead be set to a certain absolute value below the thermal dose threshold. Using these guidelines, charging device 20 may select a high power level when the available thermal dose is greater than the high power dose requirement. Charging device 20 may then select a low power level when the available thermal dose is less than the high power dose requirement. Charging device 20 may subsequently continue to charge rechargeable power source 18 with the low power level or even terminate charging once the cumulative thermal dose exceeds the thermal dose threshold.

In some examples, IMD 14 may directly adjust the power level for charging (e.g., limit the charge current) instead of relying on a change in power level at charging device 20. For example, IMD 14 may employ a circuit that may change from full-wave rectification to half-wave rectification to modify the charging characteristics of charging device 20 and/or IMD 14. In other words, IMD 14 may utilize half-wave rectification as a means to reduce the electrical current delivered to rechargeable power source 18 under typical charging conditions instead of reducing the overall power received by IMD 14. Alternatively, IMD 14 may employ other mechanisms such as current and/or voltage limiters that may limit the charging rate of rechargeable power source 18.

Although implantable rechargeable power source 18 is generally described herein, techniques of this disclosure may also be applicable to a rechargeable power source 18 that is not implanted. For example, rechargeable power source 18 may be external to the skin of patient 12 and in physical contact with the skin. Therefore, charging device 20 may select a boost period for and/or control the charging of rechargeable power source 18 based on estimated heat losses and/or a calculated cumulative thermal dose even when the power source is external to patient 12. However, boost periods, tissue models and thresholds may be modified to configure charging device 20 for external charging use.

Figure 2:
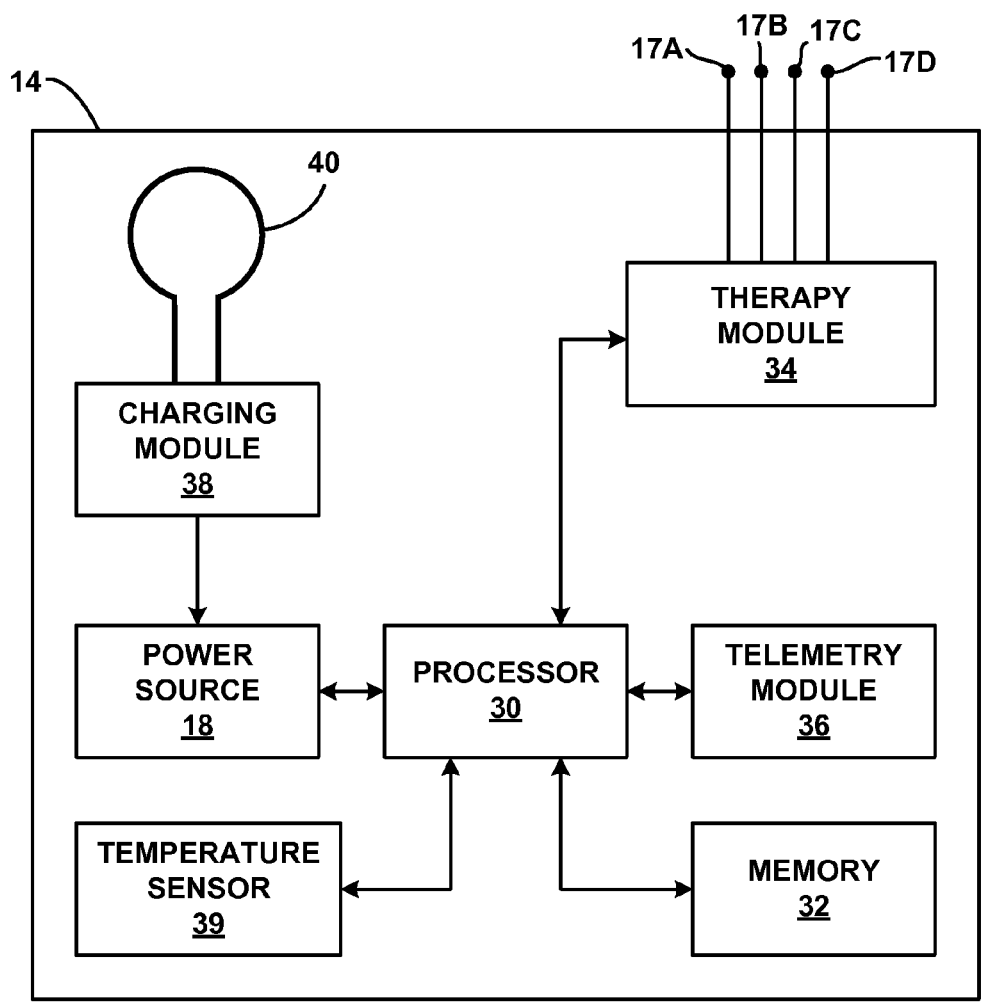
FIG. 2 is a block diagram of the example IMD of FIG. 1.

FIG. 2 is a block diagram illustrating example components of IMD 14. In the example of FIG. 2, IMD 14 includes, and may house, temperature sensor 39, coil 40, processor 30, therapy module 34, charging module 38, memory 32, telemetry module 36, and rechargeable power source 18. In other examples, IMD 14 may include a greater or fewer number of components. For example, in some examples, such as examples in which the tissue temperature is calculated from the transmitted power, IMD 14 may not include temperature sensor 39.

In general, IMD 14 may comprise any suitable arrangement of hardware, alone or in combination with software and/or firmware, to perform the various techniques described herein attributed to IMD 14 and processor 30. In various examples, IMD 14 may include one or more processors 30, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 also, in various examples, may include a memory 32, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 30, therapy module 34, charging module 38, and telemetry module 36 are described as separate modules, in some examples, processor 30, therapy module 34, charging module 38, and telemetry module 36 are functionally integrated. In some examples, processor 30, therapy module 34, charging module 38, and telemetry module 36 correspond to individual hardware units, such as ASICs, DSPs, FPGAs, or other hardware units.

Memory 32 may store therapy programs or other instructions that specify therapy parameter values for the therapy provided by therapy module 34 and IMD 14. In some examples, memory 32 may also store temperature data from temperature sensor 39, instructions for recharging rechargeable power source 18, boost period lookup tables and/or equations, tissue models, thresholds, instructions for communication between IMD 14 and charging device 20, or any other instructions required to perform tasks attributed to IMD 14. In this manner, memory 32 may be configured to store a tissue model such that processor 30 may be configured to calculate the tissue temperature surrounding IMD 14 based on the tissue model and power received by secondary coil 40 and rechargeable power source 18 over a period of time. In addition, memory 32 may store boost period information that allows processor 30 to determine an estimated heat loss, perform necessary calculations for the estimated heat loss, and select a corresponding boost period for a charging session.

Generally, therapy module 34 may generate and deliver electrical stimulation under the control of processor 30. In some examples, processor 30 controls therapy module 34 by accessing memory 32 to selectively access and load at least one of the stimulation programs to therapy module 34. For example, in operation, processor 30 may access memory 32 to load one of the stimulation programs to therapy module 34. In such examples, relevant stimulation parameters may include a voltage amplitude, a current amplitude, a pulse rate, a pulse width, a duty cycle, or the combination of electrodes 17A, 17B, 17C, and 17D that therapy module 34 uses to deliver the electrical stimulation signal. Although therapy module 34 may be configured to generate and deliver electrical stimulation therapy via one or more of electrodes 17A, 17B, 17C, and 17D of lead 16, therapy module 34 may be configured to provide different therapy to patient 12. For example therapy module 34 may be configured to deliver drug delivery therapy via a catheter. These and other therapies may be provided by IMD 14.

IMD also includes components to receive power from charging device 20 to recharge rechargeable power source 18 when rechargeable power source 18 has been at least partially depleted. As shown in FIG. 2, IMD 14 includes secondary coil 40 and charging module 38 coupled to rechargeable power source 18. Charging module 38 may be configured to charge rechargeable power source 18 with the selected power level determined by either processor 30 or charging device 20. Although processor 30 may provide some commands to charging module 38 in some examples, processor 30 may not need to control any aspect of recharging. In some examples, charging module 38 may be configured to communicate with charging device 20 such that charging module 38 may be configured to provide the functionality of telemetry module 36.

Secondary coil 40 may include a coil of wire or other device capable of inductive coupling with a primary coil disposed external to patient 12. Although primary coil 48 is illustrated as a simple loop of in FIG. 3, primary coil 48 may include multiple turns of wire. Secondary coil may include a winding of wire configured such that an electrical current can be induced within secondary coil 40 from a magnetic field. The induced electrical current may then be used to recharge rechargeable power source 18. In this manner, the electrical current may be induced in secondary coil 40 associated with rechargeable power source 18. The induction may be caused by electrical current generated in the primary coil of charging device 20 and based on the selected power level. The coupling between secondary coil 40 and the primary coil of charging device 20 may be dependent upon the alignment of the two coils. For example, the coupling efficiency increases when the two coils share a common axis and are in close proximity to each other. In other examples with different coil geometries, other relative positions of the two coils may provide greater coupling efficiency. Charging device 20 and/or IMD 14 may provide one or more audible tones or visual indications of the alignment.

Although inductive coupling is generally described as the method for recharging rechargeable power source 18, other wireless energy transfer techniques may alternatively be used. Any of these techniques may generate heat in IMD 14 such that the charging process can be controlled using the calculated cumulative thermal dose as feedback.

Charging module 38 may include one or more circuits that filter and/or transform the electrical signal induced in secondary coil to an electrical signal capable of recharging rechargeable power source 18. For example, in alternating current induction, charging module 38 may include a half-wave rectifier circuit and/or a full-wave rectifier circuit, or other rectifying schemes, configured to convert alternating current from the induction to a direct current for rechargeable power source 18. The full-wave rectifier circuit may be more efficient at converting the induced energy for rechargeable power source 18. However, a half-wave rectifier circuit may be used to store energy in rechargeable power source 18 at a slower rate. In some examples, charging module 38 may include both a full-wave rectifier circuit and a half-wave rectifier circuit such that charging module 38 may switch between each circuit to control the charging rate of rechargeable power source 18 and temperature of IMD 14.

In some examples, charging module 38 may include a measurement circuit configured to measure the current and/or voltage induced during inductive coupling. This measurement may be used to measure or calculate the power transmitted to IMD 14 from charging device 20. In some examples, the transmitted power may be used to approximate the temperature of IMD 14 and that of the surrounding tissue. This method may be used to indirectly measure the temperature of tissue in contact with the housing of IMD 14. In other examples, IMD 14 may estimate the transmitted power using the measured voltage and/or current directed to power source 18 (e.g., after charging module 38) or the charging rate of rechargeable power source 18. These current and/or voltage measurements may then be used to calculate the power transmitted to power source 18 and estimate the heat loss during charging.

Rechargeable power source 18 may include one or more capacitors, batteries, or other energy storage devices. Rechargeable power source 18 may then deliver operating power to the components of IMD 14. In some examples, rechargeable power source 18 may include a power generation circuit to produce the operating power. Rechargeable power source 18 may be configured to operate through hundreds or thousands of discharge and recharge cycles. Rechargeable power source 18 may also be configured to provide operational power to IMD 14 during the recharge process. In some examples, rechargeable power source 18 may be constructed with materials to reduce the amount of heat generated during charging. In other examples, IMD 14 may be constructed of materials that may help dissipate generated heat at rechargeable power source 18, charging module 38, and/or secondary coil 40 over a larger surface area of the housing of IMD 14.

Rechargeable power source 18 may be constructed and configured to be charged at relatively high charging rates and/or configured to be discharged to a very low voltage (e.g., approximately zero volts) without causing permanent damage to the battery. For example, rechargeable power source 18 may be a lithium-ion battery having a positive electrode (i.e., a cathode) with a positive active material and a negative electrode (i.e., an anode) with a negative active material. The positive active material and/or the negative active material, in addition to the respective positive and negative electrodes, may be selected to achieve the high charge rates and very low voltage capability.

For example, negative active electrode material may be a titanium-based material. The titanium based material may include pure titanium or a titanium alloy. In one example, the titanium alloy may be a lithium titanate material that is used as part of the negative active material of the negative electrode. The lithium titanate material may be used in place of a negative active material containing copper or a carbonaceous material such as graphite to facilitate higher charge rates and/or protect against low voltage damage to the battery. Other example negative active materials may include nickel, nickel alloys, and stainless steel.

Lithium titanate materials, as an example of titanium-based negative active materials, may allow rechargeable power source 18 to achieve desirable charging characteristics. In one example, rechargeable power source 18 may be configured to achieve high charge rates up to or greater than 10 C (i.e., attaining full charge in $\frac{1}{10}$ hours, or six minutes). The charge rate may be calculated by dividing the charging current delivered to the battery by the battery capacity. The charge rate of rechargeable power source 18 may be limited by the current that IMD 14 is capable of producing during a recharge session. In another example, rechargeable power source 18 may be fully discharged to very low voltage of approximately zero volts. After rechargeable power source 18 reaches this fully discharged voltage, rechargeable power source 18 may again be charged without any performance degradation to the battery that may otherwise occur without the lithium titanate material. Moreover, the high charge rate of rechargeable power source 18 may be achieved immediately upon recharging a fully discharged, or depleted, power source. Lithium titanate materials may also provide superior cycle life because they are so called "zero-strain" materials. Zero strain materials have crystal lattices that do not experience shrinkage or contraction with lithium doping/de-doping, making them free from strain-related degradation mechanisms.

Another advantageous feature of using a lithium titanate material is that it is believed that when used in a negative electrode of a lithium-ion battery, such materials will cycle lithium at a potential plateau of about 1.5 volts versus a lithium reference electrode. This is substantially higher than graphitic carbon, which is traditionally used in lithium ion batteries, and cycles lithium down to about 0.1 volts in the fully charged state. As a result, a battery using lithium titanate may be less likely to result in plating of lithium (which occurs at 0 volts versus a lithium reference) while being charged. Lithium plating can lead to loss in performance of lithium-ion batteries. Being free from the risk of lithium plating, cells with lithium titanate negative electrodes may also be charged at rates that exceed those with carbon negative electrodes. For example, a common upper limit for the rate of charge in lithium-ion batteries is about 0.5 C (meaning that the battery can be fully charged from the discharged state in approximately two hours). Conversely, a battery comprising lithium titanate may be charged at rates greater than 0.5 C. In some examples, a battery comprising titanate may be charged at rates up to 10 C (i.e., attaining full charge in 1/10 hour, or six minutes). Faster recharge rates may increase the functionality and/or performance of a device (e.g., IMD 14) that employs such a battery.

In addition, using a lithium titanate material instead of carbon on the negative electrode may allow rechargeable power source 18 to be charged in a constant voltage mode. In the constant voltage mode, IMD 14 (e.g., charging module 38 and/or other charging circuitry) may be configured to apply a voltage source across rechargeable power source 18 such that electrical charging current enters rechargeable power source 18 as fast as the charging circuitry and battery chemistry allows. In one example, the constant voltage may he set to a top-off voltage of rechargeable power source 18 such that a high charge rate can be maintained throughout the charge cycle of rechargeable power source 18. Top-off voltages may be selected according to the battery chemistry of rechargeable power source 18 and/or charging circuitry of IMD 14, and the top-off voltage may be selected as a voltage exceeding the final voltage (e.g., a full charge voltage) of the fully charged rechargeable power source 18. Example top-off voltages, or constant charging voltages, may be approximately 2.8 volts or approximately 3.3 volts. Charging, with a relatively high constant voltage, a battery with a carbon based negative active material of the negative electrode, for example, may severely degrade the performance of the battery.

A further advantage of a lithium titanate material is that the titanate material may avoid decomposition of organic solvents (such as propylene carbonate) commonly used in lithium-ion batteries. The lack of decomposition of organic solvents may reduce issues such as formation of gas, cell swelling, reduction of reversible battery capacity, and buildup of resistive films which may reduce available battery power.

An example lithium titanate material may include $Li_4Ti_5O_{12}$. Other lithium titanate materials which may be suitable for use as the negative active material may include one or more of the following lithium titanate spinel materials: $H_xLi_{y-x}TiO_xO_4$, $H_xLi_{y-x}TiO_xO_4$. $Li_4M_xTi_{5-x}O_{12}$, $Li_xTi_yO_4$, $Li_xTi_yO_4$, $Li[Ti_{1.67}Li_{0.33-y}M_y]O_4$, $Li_2TiO_3$, $Li_4Ti_{4.75}V_{0.25}O_{12}$, $Li_4Ti_{4.75}Fe_{0.25}O_{11.88}$, and $Li_4Ti_{4.5}Mn_{0.5}O_{12}$, and $LiM'M''XO_4$ (where M' is a metal such as nickel, cobalt, iron, manganese, vanadium, copper, chromium, molybdenum, niobium, or combinations thereof, M'' is an optional three valent non-transition metal, and X is zirconium, titanium, or a combination of these two). Note that such lithium titanate spinel materials may be used in any state of lithiation (e.g., $Li_{4+x}To_5O_{13}$, where $0 \le x \le 3$). Alternative negative active materials may be carbon, $Li_xAl$, $Li_xSn$, $Li_xSi$, $Li_xSnO$, metal nanoparticle composites (e.g., including $Li_xAl$, $Li_xSn$, $Li_xSi$, or $Li_xSnO$), or carbon-coated lithium titanate.

A positive active material of the positive electrode for rechargeable power source 18 may be a compound or material that includes lithium. The lithium included in the positive active material may be doped and undoped during discharging and charging of the battery, respectively. In one example, the positive active material may be lithium cobalt oxide ($LiCoO_2$). In another example, the positive active material may be of the form $LiCo_xNi_{(1-x)}O_2$, where x is between approximately 0.05 and 0.8. In another example, the positive active material is of the form $LiAl_xCo_yNi_{(1-x-y)}O_2$, where x is between approximately 0.05 and 0.3 and y is between approximately 0.1 and 0.3. In other examples, the positive active material may include $LiMn_2O_4$.

According to other examples, the positive active material of the positive electrode may include a material such as a material of the form $Li_{1-x}MO_2$ where M is a metal (e.g., $LiCoO_2$, $LiNiO_2$, and $LiMnO_2$), a material of the form $Li_{1-w}(M'_xM''_y)O_2$ where M' and M'' are different metals (e.g., $Li(Ni_xMn_y)O_2$, $Li(Ni_{1/2}Mn_{1/2})O_2$, $Li(Cr_xMn_{1-x})O_2$, $Li(Al_xMn_{1-x})O_2$, $Li(Co_xM_{1-x})O_2$ where M is a metal, $Li(Co_xNi_{1-x})O_2$, and $Li)Co_xFe_{1-x})O_2$)), a material of the form $Li_{1-w}(Mn_xNi_yCo_z)O_2$ (e.g., $LoCo_xMn_yNi_{(1-x-y)}O_2$, $Li(Mn_{1/3}Ni_{1/3}Co_{1/3})O_2$, $Li(Mn_{1/3}Ni_{1/3}Co_{1/3-x}Mg_x)O_2$, $Li(Mn_{0.4}Ni_{0.4}Co_{0.2})O_2$, and $Li(Mn_{0.1}Ni_{0.1}Co_{0.8})O_2$), a material of the form $Li_{1-w}(Mn_xNi_xCo_{1-2x})O_2$, a material of the form $Li_{1-w}(Mn_xNi_yCo_zAl_w)O_2$, a material of the form $Li_{1-w}(Ni_xCo_yAl_z)O_2$ (e.g., $Li(Ni_{0.8}Co_{0.15}Al_{0.05})O_2$), a material of the form $Li_{1-w}(Ni_xCo_yM_x)O_2$ where M is a metal, a material of the form $Li_{1-w}(Ni_xMn_yM_z)O_2$ where M is a metal, a material of the form $Li(Ni_{x-y}Mn_yCr_{2-x})O_4LiMn_2O_4$, a material of the form $LiM'M''_2O_4$ where M' and M'' are different metals (e.g., $LiMn_{2-y-z}Ni_y$, $Li_zO_4$, $LiMn_{1.5}Ni_{0.5}O_4$, $LiNiCuO_4$, $LiMn_{1-x}Al_xO_4$, $LiNi_{0.5}Ti_{0.5}O_4$, and $Li_{1.05}Al_{0.1}Mn_{1.85}O_{4-z}F_z$), $Li_2MnO_3$, a material of the form $Li_xV_yO_z$ (e.g., $LiV_3O_8$, $LiV_2O_5$, and $LiV_6O_{13}$), or material of the form $LiMPO_4$ where M is a metal or $LiM_x'M''_{1-x}PO_4$ where M' and M'' are different metals (e.g., $LiFePO_4$, $LiFe_xM_{1-x}PO_4$ where M is a metal, $LiVOPO_4$, and $Li_3V_2(PO_4)_3$, $LiMPO_{4x}$ where M is a metal such as iron or vanadium and X is a halogen such as fluorine, and combinations thereof.

In some examples, rechargeable power source 18 may include a lithium-ion battery that includes a positive electrode that includes a positive current collector, a first positive active material, and, in some cases, a second positive active material. The lithium-ion battery may also include a negative electrode including a negative current collector, a negative active material, and a quantity of lithium in electrical contact with the negative current collector, The first positive active material, second positive active material, and negative active materials may be configured to allow doping and undoping, of lithium ions. In other examples, the second positive, active material may be configured or selected to exhibit charging and discharging capacity below a corrosion potential of the negative current collector and above a decomposition potential of the first positive active material. In some examples, the positive and/or negative current collectors are constructed of aluminum or an aluminum alloy.

Although rechargeable power source 18, charging module 38, and secondary coil 40 are shown as contained within the housing of IMD 14, at least one of these components may be disposed outside of the housing. For example, secondary coil 40 may be disposed outside of the housing of IMD 14 to facilitate better coupling between secondary coil 40 and the primary coil of charging device 20. These different configurations of IMD 14 components may allow IMD 14 to be implanted in different anatomical spaces or facilitate better inductive coupling alignment between the primary and secondary coils.

IMD 14 may also include temperature sensor 39. Temperature sensor 39 may include one or more temperature sensors (e.g., thermocouples or thermistors) configured to measure the temperature of IMD 14. Temperature sensor 39 may be disposed internally within the housing of IMD 14, contacting the housing, formed as a part of the housing, or disposed external of the housing. As described herein, temperature sensor 39 may be used to directly measure the temperature of IMD 14 and/or tissue surrounding and/or contacting the housing of IMD 14. Processor 30, or charging device 20, may use this temperature measurement as the tissue temperature feedback to determine the cumulative thermal dose provided to tissue during charging of rechargeable power source 18. Although a single temperature sensor may be adequate, multiple temperature sensors may generate a more accurate temperature profile or average temperature of IMD 14. The various temperatures of IMD 14 may also be modeled and provided to determine the cumulative thermal dose. Although processor 30 may continually measure temperature using temperature sensor 39, processor 30 may conserve energy by only measuring temperature during recharge sessions. Further, temperature may be sampled at a rate necessary to calculate the cumulative thermal dose, but the sampling rate may be reduced to conserve power as appropriate. In other examples, temperature sensor 39 may not be used to select a boost period for charging. Instead, other indirect electrical measurements may be used to estimate the heat loss during charging.

Processor 30 may also control the exchange of information with charging device 20 and/or an external programmer using telemetry module 36. Telemetry module 36 may be configured for wireless communication using radio frequency protocols or inductive communication protocols. Telemetry module 36 may include one or more antennas configured to communicate with charging device 20, for example. Processor 30 may transmit operational information and receive therapy programs or therapy parameter adjustments via telemetry module 36. Also, in some examples, IMD 14 may communicate with other implanted devices, such as stimulators, control devices, or sensors, via telemetry module 36. In addition, telemetry module 36 may be configured to transmit the measured tissue temperatures from temperature sensor 39, for example. In some examples, the tissue temperature may be measured adjacent to rechargeable power source 18. In this manner, charging device 20 may calculate the cumulative thermal dose using the transmitted tissue temperature. In other examples, processor 30 may calculate the cumulative thermal dose and transmit the calculated cumulative thermal dose using telemetry module 36.

In some examples, processor 30 may transmit charging data to charging device 20. The charging data may include measurement data for measured electrical currents to rechargeable power source 18, voltages of rechargeable power source 18, currents within coil 40, or any other electrical parameters measured and used to determine the estimated heat loss and select the appropriate boost period. Processor 30 may command telemetry module 36 to transmit this charging data to charging device 20 or other external devices.

In other examples, processor 30 may transmit additional information to charging device 20 related to the operation of rechargeable power source 18. For example, processor 30 may use telemetry module 36 to transmit indications that rechargeable power source 18 is completely charged, rechargeable power source 18 is fully discharged, or any other charge status of rechargeable power source 18. Processor 30 may also transmit information to charging device 20 that indicates any problems or errors with rechargeable power source 18 that may prevent rechargeable power source 18 from providing operational power to the components of IMD 14.

Although IMD 14 of FIG. 2 is directed to electrical stimulation therapy, the boost period and other recharging techniques described herein may be utilized for other applications. For example, IMD 14 may be a drug pump configured to deliver a drug to patient 12. In other examples, IMD 14 may be configured as a monitor to sense one or more physiological conditions.

Figure 3:
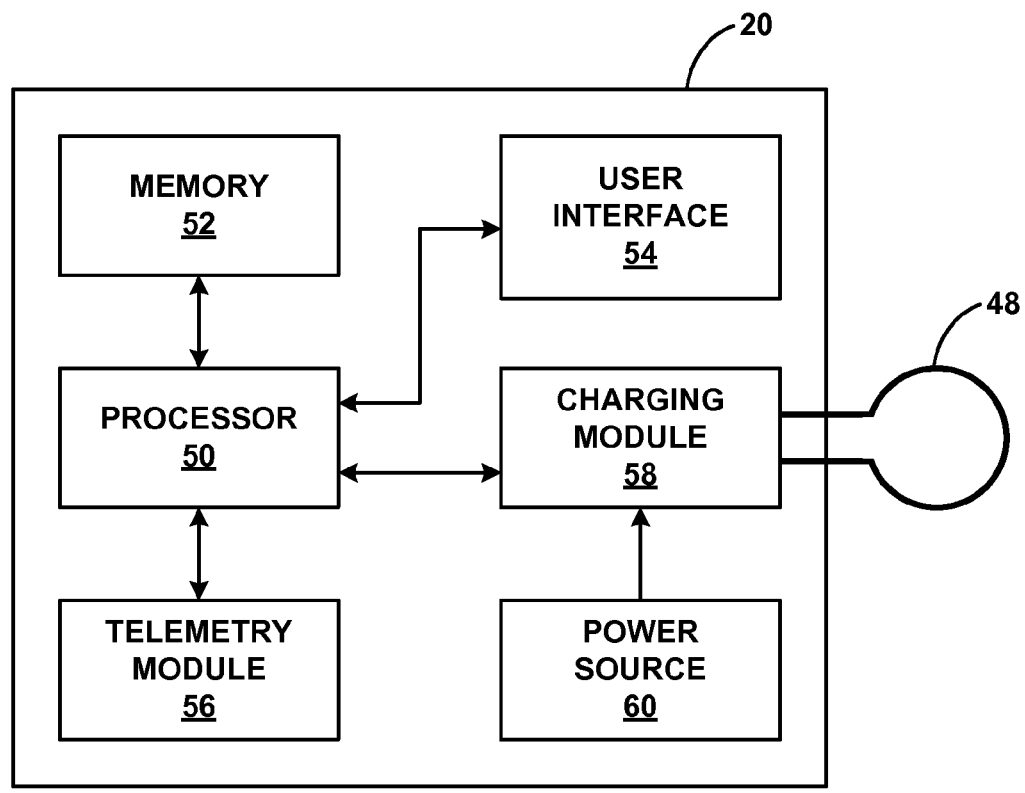
FIG. 3 is a block diagram of the example external charging device of FIG. 1.

FIG. 3 is a block diagram of the example external charging device 20. While charging device 20 may generally be described as a hand-held device, charging device 20 may be a larger portable device or a more stationary device. In addition, in other examples, charging device 20 may be included as part of an external programmer or include functionality of an external programmer. In addition, charging device 20 may be configured to communicate with an external programmer. As illustrated in FIG. 3, charging device 20 may include, and may house, a processor 50, memory 52, user interface 54, telemetry module 56, charging module 58, coil 48, and power source 60. Memory 52 may store instructions that, when executed by processor 50, cause processor 50 and external charging device 20 to provide the functionality ascribed to external charging device 20 throughout this disclosure (e.g., determine an estimated heat loss of IMD 14 and select a boost period).

In general, charging device 20 comprises any suitable arrangement of hardware, alone or in combination with software and/or firmware, to perform the techniques attributed to charging device 20, and processor 50, user interface 54, telemetry module 56, and charging module 58 of charging device 20. In various examples, charging device 20 may include one or more processors, such as one or more microprocessors, DSPs, ASICs, FPGAs, or any other equivalent integrated or discrete logic circuitry, as well as any combinations of such components. Charging device 20 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processor 50 and telemetry module 56 are described as separate modules, in some examples, processor 50 and telemetry module 56 are functionally integrated. In some examples, processor 50 and telemetry module 56 and charging module 58 correspond to individual hardware units, such as ASICs, DSPs, FPGAs, or other hardware units.

Memory 52 may store instructions that, when executed by processor 50, cause processor 50 and charging device 20 to provide the functionality ascribed to charging device 20 throughout this disclosure. For example, memory 52 may store a lookup table correlating heat loss values to respective boost periods for adapting the charging of rechargeable power source 18 to different conditions. In addition, memory 52 may include instructions that cause processor 50 to calculate cumulative thermal doses, establish thresholds, select power levels based on the cumulative thermal doses and otherwise control charging module 58, communicate with IMD 14, or instructions for any other functionality. In addition, memory 52 may include a record of selected power levels, calculated cumulative thermal doses, or any other data related to charging rechargeable power source 18. Processor 50 may, when requested, transmit any of this stored data in memory 52 to another computing device for review or further processing.

In some examples, memory 52 may be configured to store data representative of a tissue model used by processor 50 to calculate the tissue temperature based on the tissue model and power transmitted to rechargeable power source 18 over a period of time. The tissue model may indicate how temperate of tissue surrounding IMD 14 changes over time based on, i.e., as a function of, power received from primary coil 48. Therefore, processor 50 may be able to estimate the tissue temperature without direct measurement of the temperature of tissue surrounding the housing of IMD 14.

User interface 54 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processor 50 may present and receive information relating to the charging of rechargeable power source 18 via user interface 54. For example, user interface 54 may indicate when charging is occurring, quality of the alignment between coils 40 and 48, the selected power level, whether the boost period is occurring, current charge level of rechargeable power source 18, duration of the current recharge session, anticipated remaining time of the charging session, or any other information. Processor 50 may receive some of the information displayed on user interface 54 from IMD 14 in some examples.

User interface 54 may also receive user input via user interface 54. The input may be, for example, in the form of pressing a button on a keypad or selecting an icon from a touch screen. The input may request starting or stopping a recharge session, a desired level of charging, or one or more statistics related to charging rechargeable power source 18 (e.g., the selected boost period or the cumulative thermal dose). In this manner, user interface 54 may allow the user to view information related to the charging of rechargeable power source 18 and/or receive charging commands.

Charging device 20 also includes components to transmit power to recharge rechargeable power source 18 associated with IMD 14. As shown in FIG. 3, charging device 20 includes primary coil 48 and charging module 58 coupled to power source 60. Charging module 58 may be configured to generate an electrical current in primary coil 48 from voltage stored in power source 60. Although primary coil 48 is illustrated as a simple loop in FIG. 3, primary coil 48 may include multiple turns of wire or other complex geometries. Charging module 58 may generate the electrical current according to a power level selected by processor 50 based on the cumulative thermal dose. As described herein, processor 50 may select a high power level, low power level, or a variety of different power levels to control the rate of recharge in rechargeable power source 18 and the temperature of IMD 14. In some examples, processor 50 may control charging module 58 based on a power level selected by processor 30 of IMD 14. During the initial charging period, the power level may be set to a high power level that is at or near hardware limitations of system 10. Processor 50 may thus control the duration of charging with the high power level with the selected boost period based on the estimated heat loss.

Primary coil 48 may include a coil of wire, e.g., having multiple turns, or other device capable of inductive coupling with a secondary coil 40 disposed within patient 12. Primary coil 48 may include a winding of wire configured such that an electrical current generated within primary coil 48 can produce a magnetic field configured to induce an electrical current within secondary coil 40. The induced electrical current may then be used to recharge rechargeable power source 18. In this manner, the electrical current may be induced in secondary coil 40 associated with rechargeable power source 18. The coupling efficiency between primary coil 48 and secondary coil 40 of charging device 20 may be dependent upon the alignment of the two coils. Generally, the coupling efficiency increases when the two coils share a common axis and are in close proximity to each other. User interface 54 of charging device 20 may provide one or more audible tones or visual indications of the alignment.

Charging module 58 may include one or more circuits that generate an electrical signal, i.e., an electrical current, within primary coil 48. Charging module 58 may generate an alternating current of specified amplitude and frequency in some examples. In other examples, charging module 58 may generate a direct current. In any case, charging module 58 may be capable of generating electrical signals, and subsequent magnetic fields, to transmit various levels of power to IMD 14. In this manner charging module 58 may be configured to charge rechargeable power source 18 of IMD 14 with the selected power level.

The duration of time during which charging module 58 charges rechargeable power source 18 at the beginning of a charging session may be selected as a boost period based on an estimated heat loss during the charging. The initial charging period during a charge session may be performed with a high power level to charge rechargeable power source 18 in as little time as possible. However, this initial charging period, i.e., the boost period, may be limited in duration to prevent IMD 14 from heating adjacent tissue to potentially damaging temperatures. Charging module 58, or processor 50, may thus select the boost period for charging based on the estimated heat loss in IMD 14. The boost period may be longer when the heat loss is lower when targeting a predetermined current in IMD 14 due to more efficient coupling during charging.

During the boost period, and when the charging session is initially started, charging device 20 may select a high power level to charge rechargeable power source 18. As described herein, this high power level may be a power level set at the hardware limitations of the components of charging device 20 and/or IMD 14 and/or selected to achieve a targeted or desired current delivered to rechargeable power source 18. In one example, charging module 58 may initially drive primary coil 48 at approximately 2.8 W and also monitor the electrical current in rechargeable power source 18 of IMD 14. The current flowing to rechargeable power source 18 in IMD 14 may also be limited to approximately 120 mA (e.g., a hardware limitation or a targeted current level). In this manner, the 2.8 W and the 120 mA may be regarded as two limitations for system 10, and other hardware or programmed limits may similarly limit the power level for charging. The power level actually used to drive primary coil 48 may be set to whichever one of these limits is reached first. In other words, an electrical current of 120 mA flowing to rechargeable power source 18 may be reported to charging device 20 via telemetry module 56. Charging module 58 may thus reduce the power level (e.g., a high power level) such that less than 2.8 W of power is generated for coil 48 and the 120 mA limit of IMD 14 is not exceeded. Conversely, charging module 58 may drive primary coil 48 at the limit of 2.8 W, and, if the coupling efficiency between primary coil 48 and secondary coil 40 is less than ideal, the electrical current delivered to rechargeable power source 18 in IMD 14 may be less than the limit of 120 mA. Therefore, a single limitation in either charging device 20 or IMD 14 may determine the actual value of the high power level with which rechargeable power source 18 may be charged.

When selecting a power level (e.g., after the boost period is terminated), the power level that charging module 58 selects for charging may be used to vary one or more parameters of the electrical signal generated for coil 48. For example, the selected power level may specify, as parameters, a wattage, electrical current of primary coil 48 or secondary coil 40, current amplitude, voltage amplitude, pulse rate, pulse width, or any other parameter that may be used to modulate the power transmitted from coil 48. In this manner, each power level may include a specific parameter set that specifies the signal for each power level. Changing from one power level to another power level, e.g., a high power level to a low power level, may include adjusting one or more parameters. The parameters of each power level may be selected based on hardware characteristics of charging device 20 and/or IMD 14.

Power source 60 may deliver operating power to the components of charging device 20. Power source 60 may also deliver the operating power to drive primary coil 48 during the charging process. Power source 60 may include a battery and a power generation circuit to produce the operating power. In some examples, the battery may be rechargeable to allow extended portable operation. In other examples, power source 60 may draw power from a wired voltage source such as a consumer or commercial power outlet.

Although power source 60, charging module 58 are shown within a housing of charging device 20 and primary coil 48 is shown external to charging device 20, different configurations may also be used. For example, primary coil 48 may also be disposed within the housing of charging device 20. In another example, power source 60, charging module 58, and primary coil 48 may be all located external to the housing of charging device 20 and coupled to charging device 20.

Telemetry module 56 supports wireless communication between IMD 14 and charging device 20 under the control of processor 50. Telemetry module 56 may also be configured to communicate with another computing device via wireless communication techniques, or direct communication through a wired connection. In some examples, telemetry module 56 may be substantially similar to telemetry module 36 of IMD 14 described herein, providing wireless communication via an RF or proximal inductive medium. In some examples, telemetry module 56 may include an antenna, which may take on a variety of forms, such as an internal or external antenna. In some examples, charging module 58 may be configured to communicate with IMD 14 such that charging module 58 may be configured to provide the functionality of telemetry module 56.

Examples of local wireless communication techniques that may be employed to facilitate communication between charging device 20 and IMD 14 include RF communication according to the 802.11 or Bluetooth specification sets or other standard or proprietary telemetry protocols. In this manner, other external devices may be capable of communicating with charging device 20 without needing to establish a secure wireless connection. As described herein, telemetry module 56 may be configured to receive a measured tissue temperature from IMD 14. The tissue temperature may be measured adjacent to rechargeable power source 18, such as near the housing of IMD 14 or external of the housing. Although IMD 14 may measure the tissue temperature, one or more different implantable temperature sensors (e.g., standalone implantable temperature sensing devices) may independently measure the tissue temperature at different positions and transmit the temperature to charging device 20. In some examples, multiple temperature readings by IMD 14 may be averaged or otherwise used to produce a single temperature value that is transmitted to charging device 20. The temperature may be sampled and/or transmitted at different rates, e.g., on the order of microseconds, milliseconds, seconds, minutes, or even hours. Processor 50 may then use the received tissue temperature to calculate the cumulative thermal dose.

In alternative examples, the boost period may be selected by processor 50 or charging module 58 without all of the calculations needed to estimate the heat loss. For example, processor 50 may use one or more approximations to reduce the number of measurements or calculations needed to identify the appropriate boost period for charging. In other words, charging device 20 and/or IMD 14 may be designed in such a manner that several electrical parameters are known or easily approximated without needing to measure these parameters. In one example, each boost period may be selected by measuring only one electrical parameter, such as the electrical current delivered to rechargeable power source 18. In this manner, the measured electrical current may be mapped or correlated directly with a respective boost period. The electrical current may thus be a direct indicator of the coupling efficiency between the primary and secondary coils without the need for calculating the estimated heat loss. In other examples, one or more different electrical parameters may be measured and used to select a boost period for charging rechargeable power source 18. In any example, at least one electrical parameter that is reflective of changing heat losses due to power levels and/or coupling efficiency may be used to adapt the boost period to the specific charging session.

As described herein, each of the components of charging device 20 may reside within a single housing of charging device 20. In alternative examples of charging device 20, one or more components may be housed within separate housings and electrically coupled via one or more cables or wires. For example, charging module 58 and coil 48 may be disposed within a housing separate from the rest of the components of charging device 20. In this manner, charging module 58 may be tethered to the rest of the components of charging device 20 such that processor 50 may control at least a portion of the operation of charging module 58 (e.g., control the power level used to charge rechargeable power source 18).

Figure 4A:
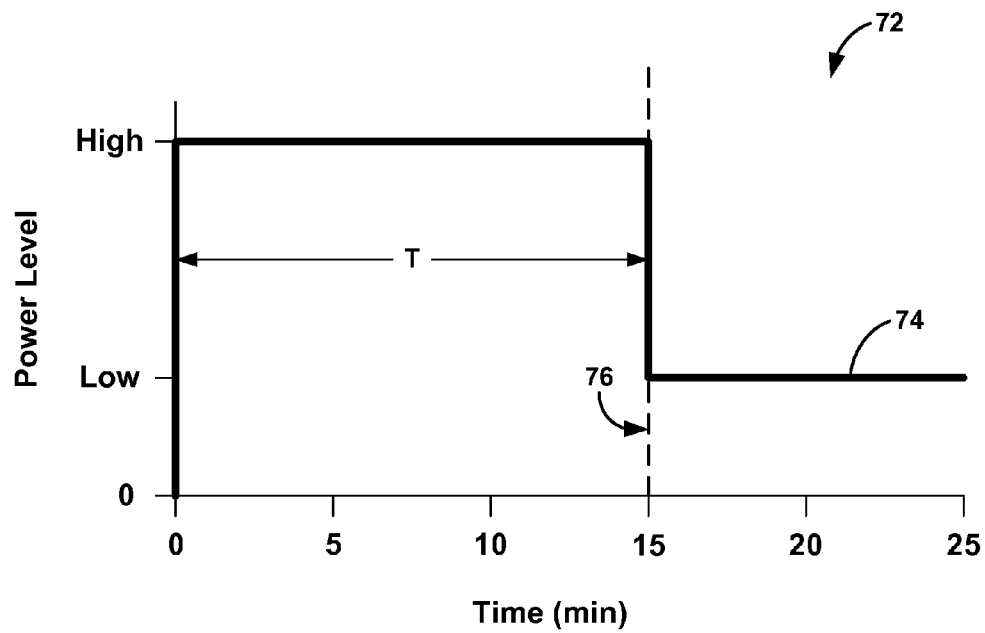
FIGS. 4A and 4B are graphs of example selected power levels for charging and an associated rechargeable power source charge level due to the selected power levels.
Figure 4B:
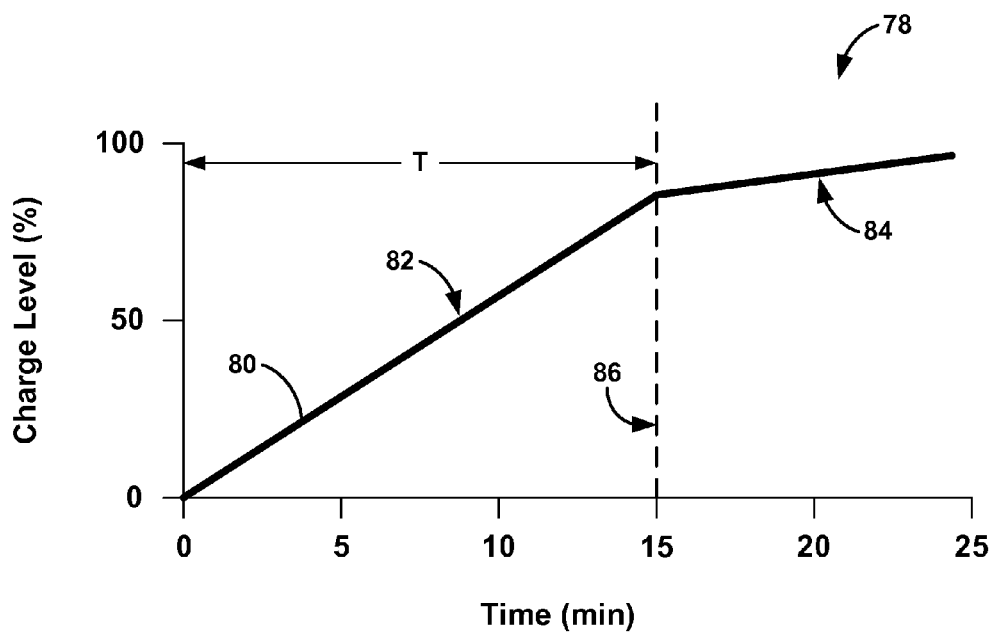

FIGS. 4A and 4B are graphs of example selected power levels for charging and an associated rechargeable power source 18 due to the selected power levels. Graphs 72 and 78 of FIGS. 4A and 4B may correspond to the changes in power level over the duration of a charge session. In other words, charge device 20 may use a high power level during the initial boost period to quickly increase the charge level in rechargeable power source 18.

As shown in FIG. 4A, graph 72 illustrates example selected power level 74 of charging device 20 for charging rechargeable power source 18. When charging is initiated, or started, at the zero minute mark, charging device 20 may select a high power level. The initial high power level 74 may be selected to charge rechargeable power source 18 at a fast rate, e.g., a "boost." This fast rate during the boost period indicated by time T may minimize the amount of time patient 12 may need to recharge rechargeable power source 18. Charging device 20 may use the high power level to transmit energy to IMD 14 until the boost period expires at charge level change 76. In the example of FIG. 4A, the boost period includes a duration of time T equal to approximately 15 minutes.

Charge level change 76 indicates a change from the high power level of the boost period to the low power level. Charging device 20 may select the low power level at charge level change 76 because the selected boost period has expired, indicating that IMD 14 should reduce the amount of heat loss. However, charging device 20 may continue to charge rechargeable power source 18 with the low power level until rechargeable power source 18 is fully charged. The low power level may be a power level at which charging can continue for a substantial amount of time, or even indefinitely, (e.g., a trickle charge) until rechargeable power source 18 is fully charged. Once rechargeable power source 18 is fully charged, charging device 20 may terminate charging by selecting a zero power level.

Graph 72 indicates high and low power levels. Although graph 72 indicates that only high and low power levels are selected, charging device 20 may select different levels of power during the charging session. Generally, the high power level may be used during the boost period, but other power levels may be used based on a user request for a lower temperature of IMD 14 or other triggers that indicate the high power level should no longer be used. Various different lower power levels may be used once the boost period has expired. In other examples, charging device 20 may only select between high and low power levels when charging rechargeable power source 18.

As shown in FIG. 4B, graph 78 illustrates charging rate 80 over time due to varying power levels selected by charging device 20. High rate 82 may be representative of the charging rate of rechargeable power source 18 when charging device 20 uses the high power level (e.g., the power level between the zero and 15 minute marks of FIG. 4A) for charging during the initial boost period. Once the boost period expires, charge rate change 86 indicates that the high power level has been terminated such that the charge rate has been lowered. Charge rate change 86 may correspond to the charge level change 76 of FIG. 4A. After charge rate change 86, the low power level induces charging rechargeable power source 18 with low rate 84. Once the charge level for rechargeable power source 18 reaches approximately 100 percent, the charge rate may be reduced to zero because the recharge session may be terminated. Although graph 78 indicates that low charge rate 84 may only take 10 minutes to complete the charge of rechargeable power source 18, the duration of low charge rate 84 may depend upon the duration of the boost period of time T. Low charge rate 84 may be required for a longer period of time for shorter boost periods, in some examples.

Figure 5A:
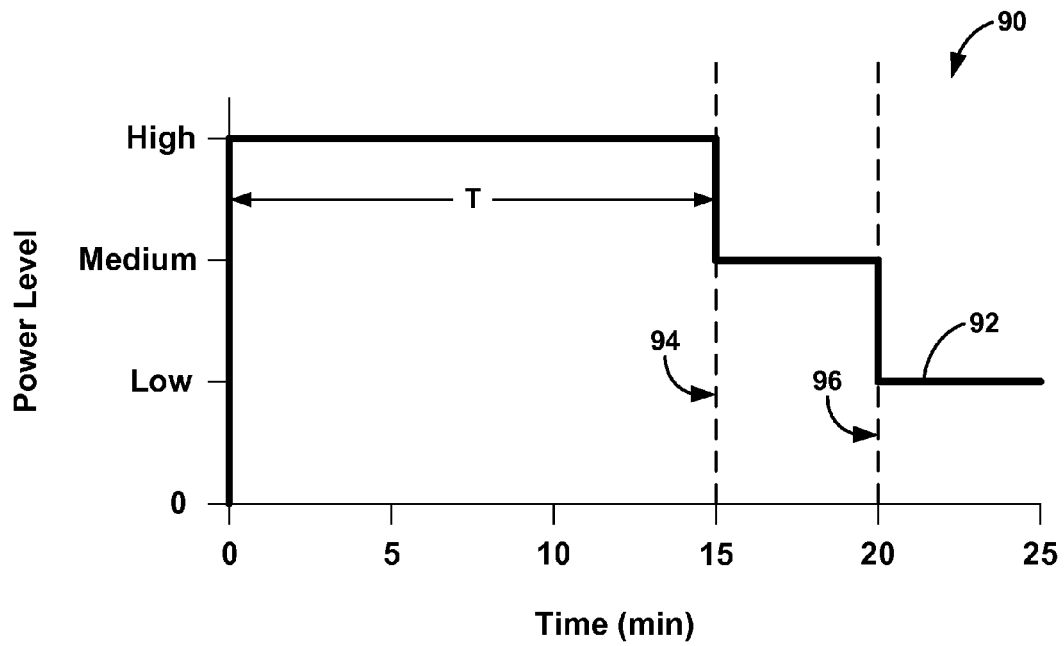
FIGS. 5A and 5B are graphs of example selected power levels for charging and an associated rechargeable power source charge level due to the selected power levels.
Figure 5B:
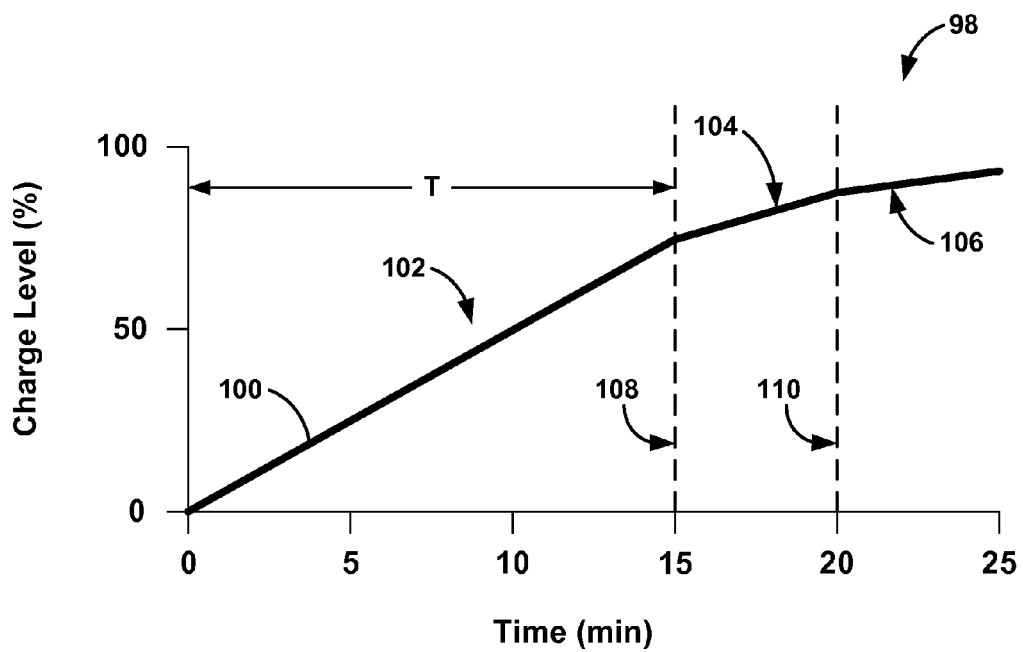

FIGS. 5A and 5B are graphs of example selected power levels for charging and an associated rechargeable power source 18 due to the selected power levels. Graphs 90 and 98 of FIGS. 5A and 5B illustrate power level changes alternative to those of FIGS. 4A and 4B. FIG. 5A illustrates three different power levels for charging and FIG. 5B illustrates the charge rate due to each selected power level. The first power level may be the high power level during the boost period. The technique of FIGS. 5A and 5B illustrates changing power levels after expiration of the boost period and prior to the cumulative thermal dose reaching the thermal dose threshold.

As shown in FIG. 5A, graph 90 illustrates example selected power level 92 of charging device 20 for charging rechargeable power source 18. When charging is initiated, or started, at the zero minute mark, charging device 20 may select a high power level and select the appropriate boost period based on the estimated heat loss at IMD 14. The initial high power level between the zero and 15 minute marks may be selected to charge rechargeable power source 18 at a fast rate, e.g., a "boost." This fast rate of the boost period may minimize the amount of time patient 12 may need to recharge rechargeable power source 18. Charging device 20 may use the high power level to transmit energy to IMD 14 until the boost period of time T has expired at charge level change 94. Depending on any changes to the coupling efficiency during the boost period, the calculated cumulative thermal dose may or may not be close to exceeding the thermal dose threshold.

Charging device 20 may calculate an available thermal dose at the conclusion of the boost period to determine when to select a lower power level for the recharge session. The available thermal dose may be calculated by subtracting the cumulative thermal dose from the thermal dose threshold. Thus, the available thermal dose may indicate the total heat that IMD 14 can still safely provide to surrounding tissue. The cumulative thermal dose may be used to adjust the power levels after the boost period has terminated.

Once charging device 20 terminates the high power level at the expiration of the boost mode, charging device 20 may select the medium power level. Charge level change 94 indicates that the power level was changed from high to medium once the boost period has expired at the 15 minute mark. Then, charging device 20 may charge rechargeable power source 18 with the medium power level between minutes 15 and 20. When the cumulative thermal dose exceeds the thermal dose threshold, charge level change 96 indicates that charging device selects the low power level for additional charging of rechargeable power source 18. Additional charging may only be performed if rechargeable power source 18 is not yet fully charged. Selected power level 92 thus changes as the cumulative thermal dose indicates the amount of heat received by tissue surrounding IMD 14. Charging device 20 may continue to charge rechargeable power source 18 with the low power level until rechargeable power source 18 is fully charged. Once rechargeable power source 18 is fully charged, charging device 20 may terminate charging by selecting a zero power level.

As shown in FIG. 5B, graph 98 illustrates charging rate 100 over time due to varying power levels selected by charging device 20. High rate 102 may be representative of the charging rate of rechargeable power source 18 when charging device 20 selects the high power level for charging (e.g., during the boost period of time T). Once the boost period expires, charge rate change 108 indicates that the charge rate has been lowered. After charge rate change 108, the medium power level induces charging rechargeable power source 18 with medium rate 104. Further, once the cumulative thermal dose exceeds the thermal dose threshold, charge rate change 110 indicates that the charge rate has been lowered. After charge rate change 110, the low power level induces charging rechargeable power source 18 with low rate 106. Once the charge level for rechargeable power source 18 reaches approximately 100 percent, the charge rate may be reduced to zero because the recharge session may be terminated.

Graph 90 of FIG. 5A indicates high, medium, and low power levels. Graph 90 indicates that charging device selects between three different power levels based on the expiration of the boost period (e.g., during time T) and the cumulative thermal dose calculated from the tissue temperature. In other examples, charging device may utilize a greater number of power levels to change the power level in smaller increments. Therefore, charging device 20 may provide finer control of the recharge rate and the temperature of IMD 14 during the charging session. The finer control of power may allow charging device 20 to gradually change the temperature of IMD 14, e.g., reduce the temperature of IMD 14 such that the cumulative thermal dose does not exceed the thermal dose threshold even after charging stops. This may be particularly useful in situations where the boost period could have been longer due to increased coupling efficiency after the boost period started when targeting a current value in IMD 14 (e.g., the current of IMD 14 is used to limit the charging power level).

In FIGS. 4A, 4B, 5A, and 5B, charging device 20 selects the low charge level even after the cumulative thermal dose exceeds the thermal dose threshold. In these cases, the low charge level may only cause negligible heating of IMD 14. In other words, the heat produced in IMD 14 during the application of the corresponding low charge rate may cause an insignificant increase to the cumulative thermal dose because the temperature is similar to that of normal body temperature. However, in other examples, the low charge level may still generate heat in IMD 14 and contribute to the cumulative thermal dose. In this case, charging device 20 may terminate the charging of rechargeable power source 18 (e.g., select a zero power level).

Figure 6A:
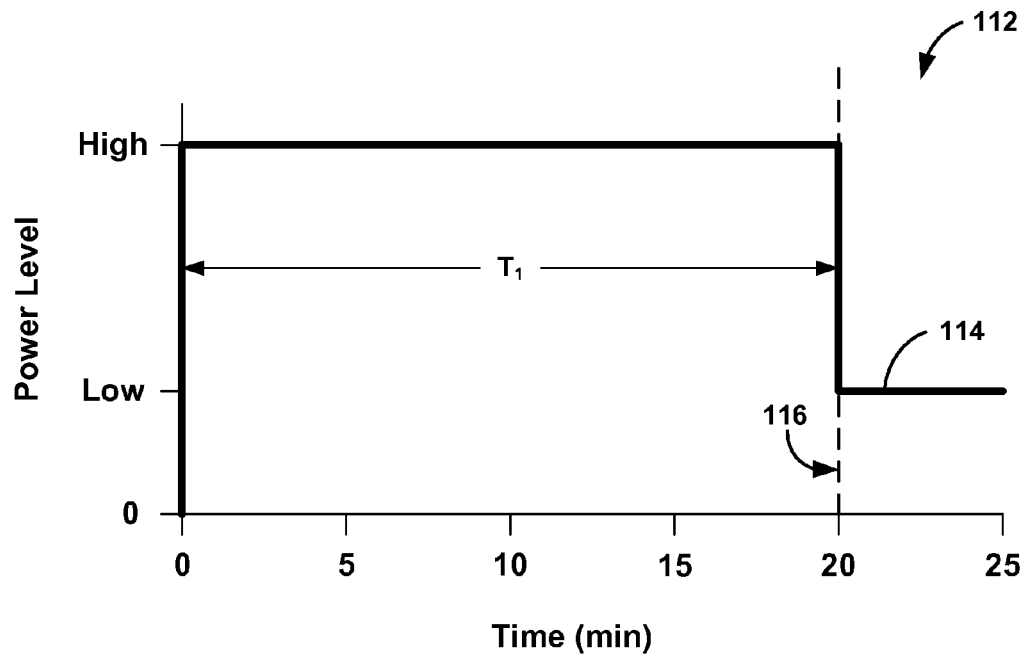
FIGS. 6A and 6B are graphs of example charge power levels over time for different boost periods selected based on estimated heat losses during initial charging.
Figure 6B:
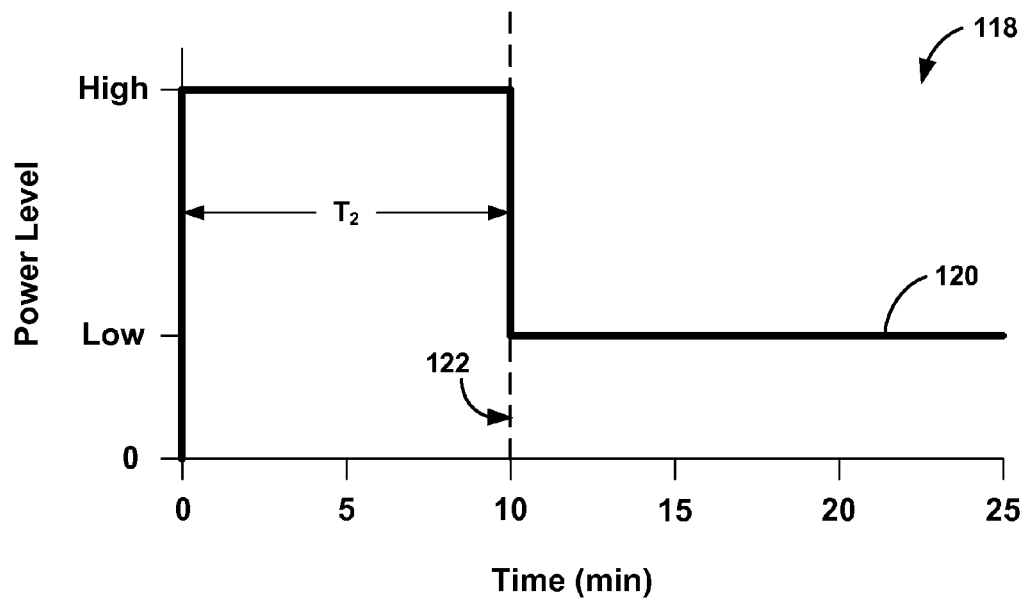

FIGS. 6A and 6B are graphs of example charge power levels over time for different boost periods selected based on estimated heat losses during initial charging. FIGS. 6A and 6B may be substantially similar to FIG. 4A. However, FIGS. 6A and 6B illustrate how the boost period may change for different estimated heat losses at IMD 14. Graph 112 of FIG. 6A may indicate a boost period selected with a low heat loss and graph 118 of FIG. 6B may indicate a boost period selected with a high heat loss. The durations of each boost period are merely exemplary and may vary in other examples.

As shown in FIG. 6A, graph 112 illustrates example selected power level 114 of charging device 20 for charging rechargeable power source 18. When charging is initiated, or started, at the zero minute mark, charging device 20 may select a high power level. The initial high power level 114 may be selected to charge rechargeable power source 18 at a fast rate, e.g., a "boost." This fast rate during the boost period of 20 minutes indicated by time $T_1$ may minimize the amount of time patient 12 may need to recharge rechargeable power source 18. Upon the expiration of boost period $T_1$, charge level change 116 indicates a change from the high power level of the boost period to the low power level. Charging device 20 may continue to charge rechargeable power source 18 with the low power level until rechargeable power source 18 is fully charged.

As shown in FIG. 6B, graph 118 illustrates example selected power level 120 of charging device 20 for charging rechargeable power source 18. When charging is initiated, or started, at the zero minute mark, charging device 20 may select a high power level. The initial high power level 120 may be selected to charge rechargeable power source 18 at the fast rate, e.g., a "boost." This fast rate during the boost period of 10 minutes indicated by time $T_2$ may minimize the amount of time patient 12 may need to recharge rechargeable power source 18, but boost period $T_2$ is less than boost period $T_1$ of FIG. 6A. This difference may occur because the estimated heat loss of IMD 14 in FIG. 6B is greater than the heat loss determined for the charging session of FIG. 6A. Upon the expiration of boost period $T_2$, charge level change 120 indicates a change from the high power level of the boost period to the low power level. Charging device 20 may continue to charge rechargeable power source 18 with the low power level until rechargeable power source 18 is fully charged. Since boost period $T_2$ is shorter than boost period $T_1$, charging device 20 may need to charge rechargeable power source 18 for a longer duration at the low power level to achieve a full charge than would be needed after the longer boost period of FIG. 6A.

Generally, once the boost period is selected based on the initially determined estimated heat loss, charging device 20 may continue to charge rechargeable power source 18 until the boost period expires (e.g., elapses, terminates, or stops). In other words, the boost period may not change in duration until the originally selected boost period duration expires. In some examples, charging device 20 may be configured to adjust the duration of the boost period while the boost period is being used to charge rechargeable power source 18. By adjusting the duration of the boost period, charging device 20 may compensate for changes to heat loss from increases or decreases in coupling efficiency.

As described herein, charging device 20 and/or IMD 14 may determine the estimated heat loss at the beginning of the charging session. However, charging device 20 may re-calculate or re-determine the estimated heat loss one or more times during the boost period. For example, charging device 20 may re-calculate the heat loss at a predetermined time after starting the boost period. The predetermined period may be a set time irrespective of the selected boost period. For example, charging device 20 may re-calculated the heat loss one minute after the boost period starts to check for a change in coupling efficiency. In other examples, the predetermined period may be set to a portion of the selected boost period. For example, charging device 20 may re-calculate the heat loss after 20 percent of the boost period has expired. These predetermined periods may be shorter or longer in other examples. Alternatively, charging device 20 may re-calculate the heat loss several times, periodically, or continuously during the boost period.

Re-calculating the estimated heat loss may allow charging device 20 to identify any changes to the coupling efficiency between the primary and secondary coils. If the estimated heat loss is greater than the previous calculation, charging device 20 may decrease the boost period duration of time. If the estimated heat loss is less than the previous calculation, charging device 20 may increase the boost period duration of time. In some examples, charging device 20 may use an equation to increase or decrease the boost period based on the subsequent estimated heat loss. In other examples, charging device 20 may select subsequent boost periods from a different lookup table. This lookup table may provide a new boost period based on the new estimated heat loss, the previously selected boost period, the elapsed time of the current boost period, or some combination thereof. In alternative examples, a cumulative thermal dose may be calculated for the boost period and used to determine the remaining boost period for the high power level of charging. This re-evaluation of the boost period may be computationally intensive and provide a more accurate boost period based on changing charging conditions.

Figure 7:
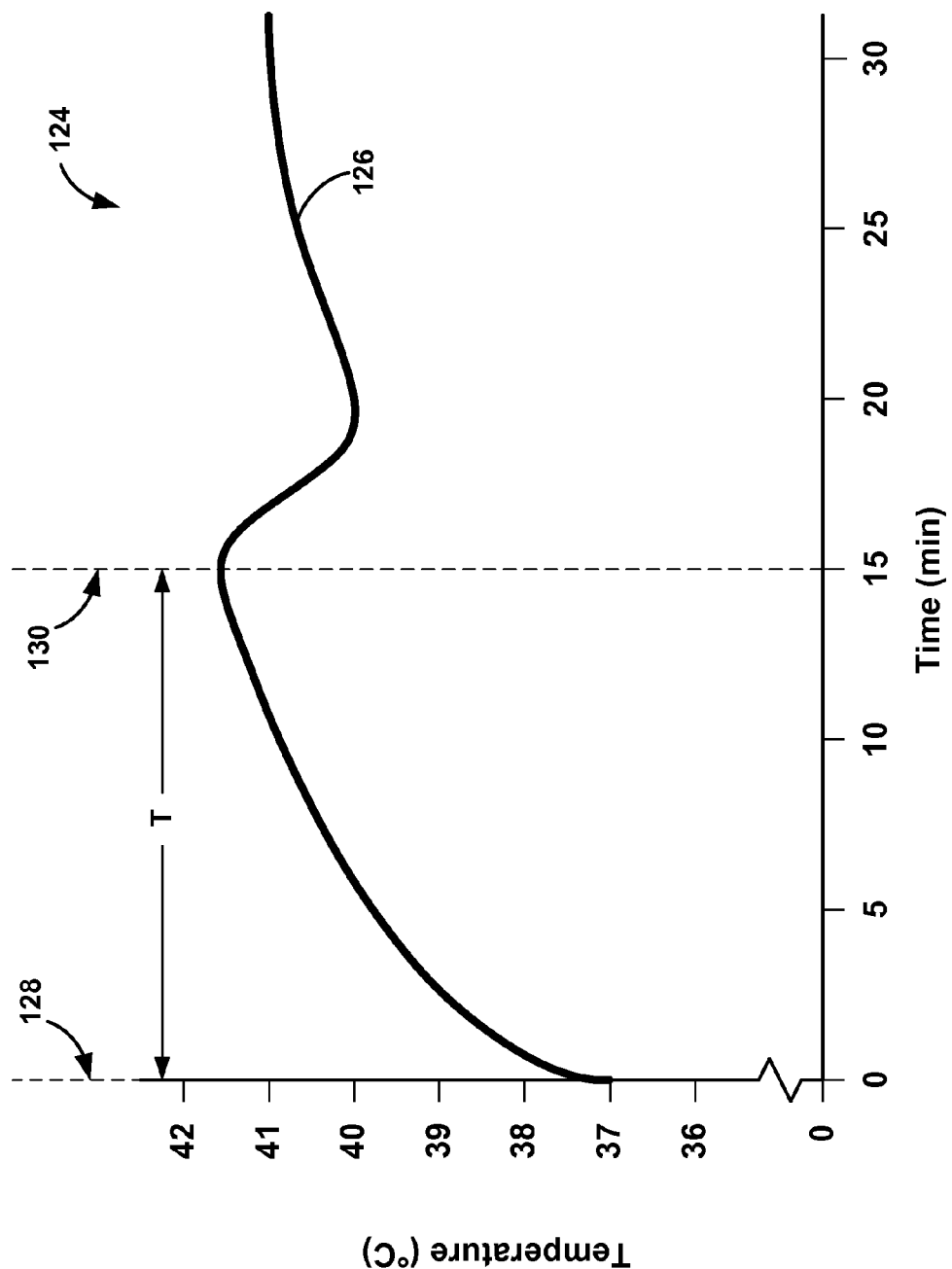
FIG. 7 is a graph of example temperatures generated in a patient during IMD recharging during and after a boost period of charging.

FIG. 7 is a graph of example temperatures generated in a patient during IMD 14 recharging during and after a boost period of charging. As shown in FIG. 7, graph 124 includes temperature 126 over time during recharging of rechargeable power source 18. Graph 124 may be representative of the tissue temperatures surrounding IMD 14 during a charging session of example FIGS. 4A and 4B. This temperature may be measured within IMD 14, on the housing of IMD 14, or within tissue surrounding IMD 14. Alternatively, the temperature may be calculated based on power transmitted to IMD 14 and a tissue model of how tissue would respond based on the power transmitted over time. Therefore, temperature 126 may be representative of how temperatures in tissue surrounding and/or contacting the housing of IMD 14 may change when rechargeable power source 18 is being recharged with given levels of recharge power. In other examples, temperature 126 may be limited to lower temperatures or allowed to reach greater temperatures (e.g., up to 42 degrees Celsius or up to 43 degrees Celsius).

Graph 124 may indicate how temperature 126 changes when charging device 20 initially charges rechargeable power source 18 at the high power level during the boost period of time T and at a low power level after the boost period expires. Once charging of rechargeable power source 18 begins at the zero minute mark (power level change 128), temperature 126 begins to increase from approximately 37 degrees Celsius. Because charging device 20 transmits power at a high power level during the boost period, rechargeable power source 18 may charge at a fast rate and the temperature of IMD 14 and surrounding tissue may increase at a relatively high rate as compared to slower charging rates with lower transmitted power levels. Temperature 126 may reach a certain magnitude (e.g., approximately 41.5 degrees Celsius) based on the transmitted power and the ability of the tissue to dissipate heat.

Time T may indicate the duration of the selected boost period based on the estimated heat loss in IMD 14. If charging device 20 or IMD 14 calculates the cumulative thermal dose, the cumulative thermal dose may be calculated using a variety of different techniques that indicate this total amount of heat. For example, temperature 126 may be integrated over time to calculate the cumulative thermal dose in degree-minutes. The cumulative thermal dose may be the area under the curve of temperature 126 for a desired time period and may be representative of the total amount of heat delivered to tissue from IMD 14 over that time period. Since the normal physiological temperature of tissue is approximately 37 degrees Celsius, temperature 126 may only be integrated for temperatures about this 37 degree Celsius floor. However, the cumulative thermal dose may be calculated using any temperature as a floor as long as the thermal dose threshold, or any other thresholds, are established using this floor temperature as well. For example, the starting temperature or the temperature floor for calculating the cumulative thermal dose may be lower or higher than 37 degrees due to the location of IMD 14, environmental conditions surrounding patient 12, or even health conditions of patient 12 (e.g., patient 12 may have a fever and increased body temperature).

In other examples, the cumulative thermal dose may be calculated using alternative techniques. For example, charging device 20 may average temperature 126 for each segment of time (e.g., each minute) and sum the average temperatures for each minute to calculate the cumulative thermal dose. Alternatively, the cumulative thermal dose may be calculated using more complex equations to account for the effect to tissue at different magnitude of temperatures, e.g., weight time differently at different temperatures.

As temperature 126 increases, the effects of each incremental change in temperature may cause a disproportional increase in undesirable tissue effects and decrease patient comfort. In other words, each degree change may exponentially decrease the amount of time tissue can safely be exposed to that temperature. For example, it may be safe to expose tissue to 41 degrees Celsius for 4 hours, but a small increase in temperature to 43 degrees may decrease the safe exposure time to only 30 minutes. In this manner, the cumulative thermal dose may be calculated to account for the non-linear relationship between temperature and undesirable side effects over time.

Once the boost period expires, charging device 20 may decrease the charging power to a low power level at power level change 130. In the example of FIG. 7, the boost period expires after a duration of approximately 15 minutes after beginning to charge rechargeable power source 18 with the high power level. The low power level after the boost period may thus decrease the rate that rechargeable power source 18 is charged and temperature 64 may decrease with this decreased transmitted power until the transmitted power again increases temperature 64 slightly over time. In other examples, charging device 20 may select a medium power level between the high power level and the low power level to charge rechargeable power source 18 without the increased temperatures during the boost period and at a higher rate than the low power level. In this case, charging device 20 and/or IMD 14 may calculate the cumulative thermal dose and compare it to the cumulative thermal dose threshold. In any case, charging device 20 may select the power level for charging rechargeable power source 18 after the boost period based on the cumulative thermal dose calculated using temperature 126.

Temperature 126 of graph 124 is only an example of tissue temperature changes due to charging rechargeable power source 18 in IMD 14. In other examples, temperature 126 may change at faster or slower rates. In addition, temperature 126 may plateau at lower temperatures, plateau at higher temperatures, or not plateau at all during the recharge session. In this manner, the thermal dose threshold, method of calculating the cumulative thermal dose, and other variables for managing the cumulative thermal dose received by patient 12 may be adjusted based on the specific characteristics of charging device 20, IMD 14, and even patient 14.

FIGS. 8A and 8B are example lookup tables 132A and 132B with boost periods 137 corresponding to different estimated heat loss values 134 and corresponding charging currents 135 in IMD 14. In addition, lookup tables 132A and 132B include charge rate values 136 that indicate relative charging rates at the corresponding charging currents 135. As described herein, charging device 20 and/or IMD 14 may store a lookup table so that a boost period may be selected that corresponds to an estimated heat loss in IMD 14. In the example of FIGS. 8A and 8B, respective lookup tables 132A and 132B include different boost periods 137 that each correspond to one of the different heat loss values 134. In some examples, lookup tables 132A and 132B may be stored as a single lookup table.

Charging currents 135 and charge rate values 136 are specific to one example of IMD circuitry and capacity of the battery (e.g., rechargeable power source 18). Table 132A includes smaller heat loss values between 1.0 and 2.0 Watts (W), and table 132B includes larger heat loss values between 2.8 and 13.0 W. As the heat loss values 134, charging currents 135, and charge rate values 136 increase, the corresponding boost periods 137 decrease.

Charging device 20 and/or IMD 14 may utilize lookup tables, such as example lookup tables 132A and 132B, for selecting the appropriate boost period that corresponds to the determined estimated heat loss from IMD 14. For example, using lookup table 132A, charging device 20 may determine that the estimated heat loss at the beginning of the charging session is approximately 1.4 Watts (W). Charging device 20 may thus select the corresponding boost period of 940 seconds (e.g., 15 minutes and 40 seconds). In other words, the boost period for charging with a high power level may be 940 seconds in duration if the estimated heat loss is determined to be 1.4 W.

Charging currents 135 are example charging currents that may occur within IMD 14 at the corresponding heat losses of heat loss values 134. Each of charging currents 135 may be created when charging of rechargeable power source 18 begins. Higher charging currents may induce greater heat loss and result in a shorter boost period. For example, a charging current of 83.6 milliamps (mA) may correspond to a heat loss of approximately 1.0 W and an available boost period of approximately 1820 seconds. For comparison, a charging current of 122.0 mA may correspond to a heat loss of approximately 1.6 W and an available boost period of approximately 720 seconds. The higher charging current within IMD 14 may be caused by greater power generated from the primary coil in the charging device and lead to greater heat loss from IMD 14 and a shorter available boost period.

The charging currents 135 provided in FIG. 8A (and FIG. 8B) may be applicable for one configuration of charging circuitry and batteries of IMD 14. For example, different charging circuitry, battery capacity, IMD geometry, materials, and other variables may contribute to different charging currents 135 and heat loss values 134 in other examples. In addition, lower coupling efficiency between the primary and secondary coils may result in lower charging currents 135 for the same power produced by the primary coil. Moreover, IMD 14 may limit the charge current in some examples. IMD 14 may be configured to limit the charging current based on battery capacity, material selections, or other design considerations. For example, IMD 14 may be configured to limit the charging current to 120 mA, 140 mA, or any other limit selected for the specific configuration of IMD 14. The example charging currents 135 of FIGS. 8A and 8B may correspond to a rechargeable power source 18 having a negative electrode with a lithium titanate negative active material to achieve high charge rate (such as a charge rate of 10 C in table 132B) and/or allow very low discharge voltages.

Charge rate values 136 correspond to the relative charging rate for a particular battery capacity and charging currents 135 applied to the battery. Charge rate values 136 may be calculated by dividing the charging current by the battery capacity. Therefore, higher charging currents are needed to maintain equal charging rates in a larger capacity battery. In the example of FIGS. 8A and 8B, the battery may have an 85 milliampre-hour (mAh) capacity and the IMD has particular circuitry, dimensions, and materials that result in the example charging currents 135. Higher charge rate values 136 may provide faster recharging of rechargeable power source 18, but the duration of the boost period at these higher charge rates may be limited due to the higher heat loss by the IMD.

In one example, charging device 20 may control charging module 58 to charge rechargeable power source 18 at a charge rate greater than approximately 0.5 C. In other examples, charging device 20 may control charging module 58 to charge rechargeable power source 18 at a charge rate greater than approximately 1.0 C, e.g., between approximately 1.0 C and 2.0 C. These example charge rates are shown in table 132A. In some examples, charging device 20 may control charging module 58 to charge rechargeable power source 18 at a charge rate greater than approximately 5.0 C, e.g., between approximately 5.0 C and 10.0 C. These example charge rates are provided in table 132B. Charge rates greater than 10.0 C may also be utilized in other examples. In any example, the charge rates and corresponding boost periods may allow for relatively fast charging of rechargeable power source 18. As described above, high charge rates may be facilitated by charging at a constant voltage greater than a full charge voltage of rechargeable power source 18. In some examples, controlling charging module 58 may include outputting a charging signal targeted to achieve the desired charging rate. Although charging device 20 may control charging module 58 to charge rechargeable power source 18 at a certain charge rate, charging module 58 may instead control the charge rate based at least in part on the charging signal from charging device 20.

For example, at a charge rate of approximately 10.0 C shown in table 132B, the boost period of this high charge rate may be limited to approximately 6 seconds due to the generated heat that is lost to the patient. In other examples, boost periods may be longer at high charge rates when IMD 14 is constructed with different materials and/or of different dimensions.

Lookup table 132A provides boost periods 136 for the range of heat loss values 134 between approximately 1.0 W and 2.0 W. These heat loss values correspond to a range of boost periods between 450 seconds and 1820 seconds. If the heat loss is less than 1.0 W or greater than 2.0 W (e.g., the higher values of heat loss values 134), charging device 20 may select the corresponding longest or shortest boost period if the determined heat loss falls outside of the range of lookup table 132A. For example, even if the estimated heat loss is greater than 2.0 W, the boost period of 450 seconds may still be used. These maximum and minimum boost periods may thus be selected for best case and worst case heat loss scenarios. In other examples, charging device 20 may extrapolate boost period durations for estimated heat losses falling outside of the range of lookup table 132A. Charging device 20 may additionally extrapolate boost periods when the estimated heat loss falls between any two heat loss values 134.

Alternatively, lookup table 132B of FIG. 8B may be used for estimated heat losses greater than 2.0 W. Lookup table 132B may provide boost periods 137 between approximately 216 and 6 seconds at respective charge rates 136 between approximately 2.4C and 10.0 C. Any look up table stored by IMD 14 to provide boost periods for corresponding heat losses may be limited to the possible charging currents available to IMD 14. Therefore, boost period durations may be limited by the charging limitations of IMD 14 and/or rechargeable power source 18. Higher charge rate values 136 of lookup table 132B may allow faster recharging of rechargeable power source 18 unless the boost period is limited by the allowable heat discharged to patient 12.

In some examples, each of boost periods 136 may correspond to a range of heat loss values. For example, if the estimated heat loss is greater than 1.3 W but less than or equal to 1.4 W, the boost period of 940 seconds corresponding to 1.4 W may be selected. In this manner, charging device 20 may round to the shorter boost period 136. This rounding to a shorter boost period may limit the potential for tissue damaging temperature levels from IMD 14. The values of heat loss values 134 and boost periods 136 are merely examples and may be different for different patients, implant locations, types of IMD 14, patient comfort levels, or any other variables. In this manner, the estimated heat loss values 134 of lookup table 132 may be lower than 1.0 W or greater than 2.0 W. In addition, the heat loss values of lookup values may be presented in different units or provided as absolute heat values instead of heat transfer rates. Alternatively, IMD 14 may interpolate between boost periods 137 for estimated heat losses between heat loss values 134 provided by lookup tables 132A or 132B.

The boost period may have a duration between one or more seconds to greater than 60 minutes, depending upon the heat loss and characteristics of the IMD. In one example, the boost period may have a duration between approximately 5 minutes and approximately 35 minutes. In another example, the boost period may have a duration between approximately 10 minutes and approximately 25 minutes. In the example of FIG. 8A, the boost period may be between 450 seconds (7 minutes and 30 seconds) and 1820 seconds (30 minutes and 20 seconds). Alternatively, the boost period may be selected to be less than 5 minutes (as shown in example lookup table 132B of FIG. 8B) or greater than 35 minutes. In some examples, the longest and shortest boost periods of lookup tables 132A or 132B may be provided for any estimated heat losses falling outside of the heat loss values provided by the respective lookup tables. In other words, the boost period duration may be capped to a shortest boost period during worst case heat loss scenarios (e.g., higher heat loss) and a longest boost period during best case heat loss scenarios (e.g., lower heat loss).

In some examples, boost periods 137 of lookup tables 132A and 132B may be adjusted according to one or more patient preferences. For example, patient 12 may be sensitive to increased temperate from IMD 14 and desire a lower temperature of IMD 14 during charging. Charging device 20 may thus reduce each of boost periods 137 according to the patient preference. Conversely, charging device 20 may increase the boost periods 137 if patient 12 desires shorter charge sessions and can tolerate higher temperatures of IMD 14 during the charging session.

In one example, boost periods 137 may be set to three different durations. Patient 12 may provide an input that specifies one of three different boost period preferences. For example, patient 12 may select between a "cool" (short boost period), "average" (average boost period), or "warm" (long boost period) for subsequent charging sessions. In other examples, patient 12 may provide input that provides finer control over the adjustments of boost periods 137. In some examples, the lookup table may provide the longest possible boost periods 137 possible for each heat loss value 134 by default. The patient preference may then reduce each boost period according to the patient's preference. Patient 12 may provide the preference input via charging device 20 or another programming device that communicates with charging device 20 and/or IMD 14.

In some examples, the duration of boost periods 137 may be determined based on a starting temperature adjacent IMD 14 of approximately 37 degrees Celsius. However, boost periods 137 may be determined, or adjusted, to compensate for lower or higher starting temperatures. For example, temperature sensor 39 may provide the initial starting temperature of IMD 14 prior to starting the charging session. In one example, a higher starting temperature (e.g., patient 12 may have a fever) may be used to reduce the duration of boost periods 136 such that the heat loss to patient 12 during the boost period does not exceed the desired threshold. In this manner, the boost period described herein may be determined, at least in part, based on a measured temperature of IMD 14 prior to starting a charging session.

Estimated heat loss values 134, charging currents 135, and boost periods 137 of FIGS. 8A and 8B may correspond to different charging signals at similar coupling efficiencies between the primary and secondary coils. Therefore, lower coupling efficiencies may result in higher heat losses at the same charging currents (or lower charging currents for the same heat losses). Conversely, higher coupling efficiencies may result in lower heat losses at the same charging currents (or higher charging currents for the same heat losses). In some examples, tables 132A and 132B may be generated based on low coupling efficiencies to establish an increased safety factor when determining the duration of the boost period.

Figure 9A:
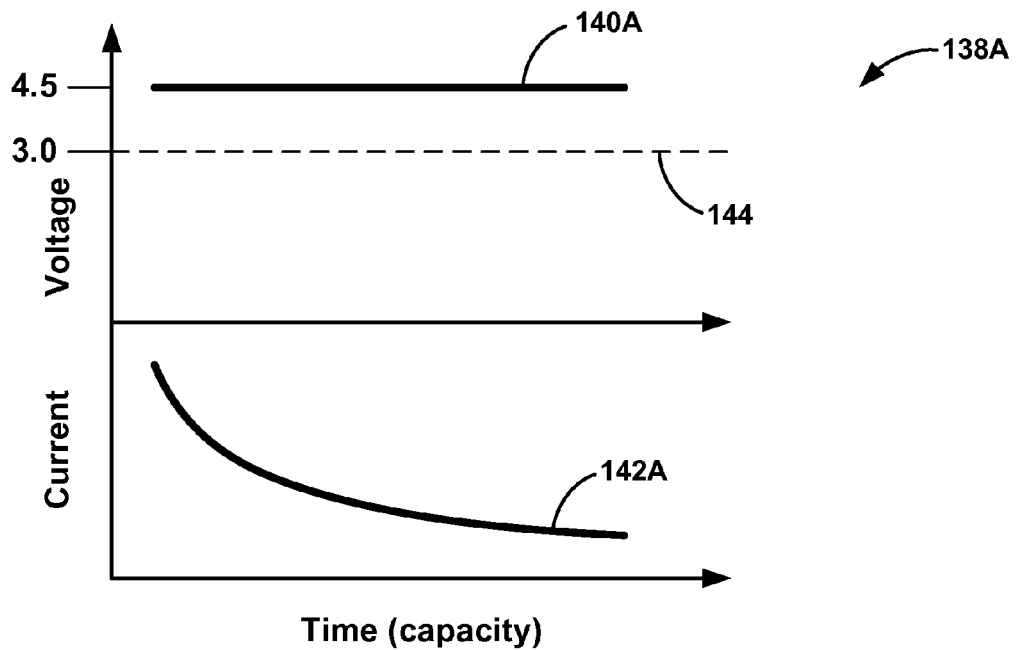
FIGS. 9A and 9B are example graphs of constant voltage and constant current charging routines of a rechargeable power source.
Figure 9B:
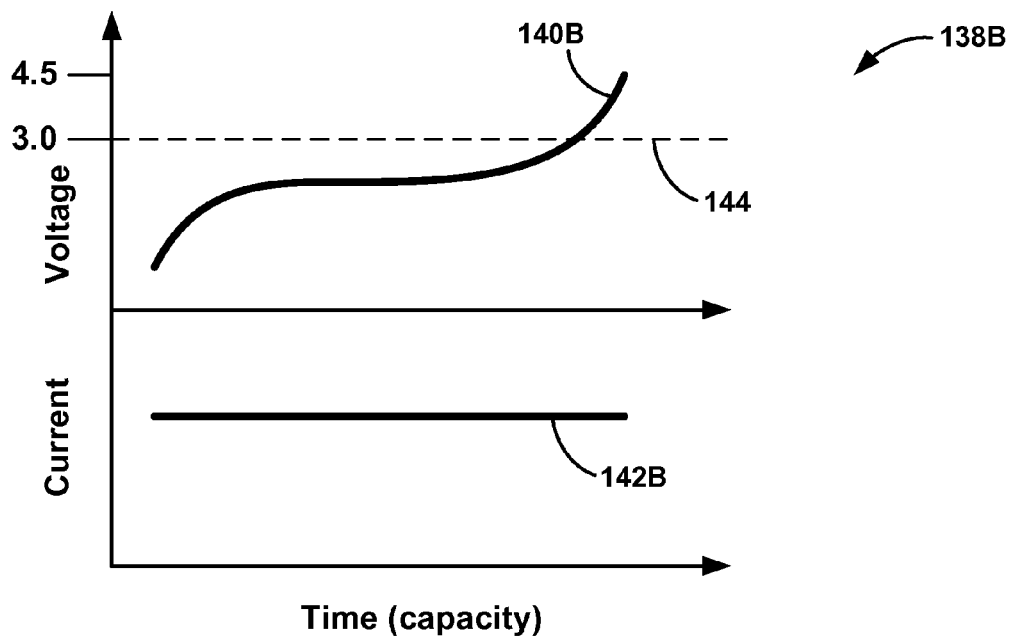

FIGS. 9A and 9B illustrate example charging routines with respect to charging voltage and charging current over time. FIG. 9A is an example illustration of graph 138A illustrating one example theoretical charging routine or algorithm. As shown in FIG. 9A, a constant voltage charging routine may be utilized in which IMD 14 controls the charging voltage at level 140A (e.g., a constant voltage). Voltage level 140A is greater than the expected final charge voltage 144 (e.g., a full charge voltage) of rechargeable power source 18 (i.e., the battery). In other words, final charge voltage 144 or a full charge voltage would be the voltage of the battery (e.g., rechargeable power source 18) when the battery has been fully charged to a full capacity. Voltage level 140A may be referred to as a top-off voltage in some examples. When charging is performed at a constant voltage, the charging current level 142A may initially be high to meet the high constant voltage and begin charging rechargeable power source 18 quickly. In some cases, charge rates may be 10 C or greater. Charging current level 142A may then decrease with time as the capacity of the battery increases. In one example, charging module 38 may control recharging of rechargeable power source 18 at the constant voltage (e.g., voltage level 140A) greater than a full charge voltage (e.g., final charge voltage 144) of rechargeable power source 18, in another example, charging device 20 may control charging module 38 to charge rechargeable power source 18 at a constant voltage greater than a full charge voltage of rechargeable power source 18.

In an example in which the final charge voltage 144 of the battery the open circuit voltage of the fully charged battery) is approximately 3.0 volts, IMD 14 may charge the battery at a constant voltage of up to approximately 4.5 volts as shown in FIG. 9A. The 1.5 volt difference between the desired final charge voltage 144 and the charging voltage level 140A represents the approximate potential of the negative electrode. This charging routine may result in an overpotential (e.g., an overpotential of greater than 70 millivolts) for at least a portion of the charging operation. In other examples, the final charge voltage and the constant charging voltage may be different, but the charging voltage is generally greater than the final charge voltage of the battery. In this manner, charging of rechargeable power source 18 may be accomplished at a relatively quick rate as compared to charging of batteries using conventional negative electrode materials (e.g., carbon, etc.).

To determine the point at which charging of the battery as shown in FIG. 9A should be terminated, various cutoff criteria may be utilized. Batteries using lithium titanate active materials on the negative electrode may experience a relatively abrupt increase in cell voltage at the end of charging. This abrupt increase in cell voltage may correspond to a relatively abrupt decrease in negative electrode potential that is not generally present in batteries using carbon or other conventional negative active materials (since the potential of the negative electrode at this point is already near zero volts). Identification of this point during charging may be used as an indication that charging is nearly complete and/or that charging should be stopped. Various other techniques may also be used for determining when charging of the battery (e.g., rechargeable power source 18 should be stopped. For example, charging module 38 or other circuitry of IMD 14 may stop charging of the battery in response to determining that a predetermined amount of time has elapsed from initiating the charging period. In another example, charging module 38 or other circuitry of IMD 14 may stop (or control termination of) charging of the battery in response to determining that the current of the battery falls below a predetermined threshold (i.e., charging current level 142A may fall below a predetermined threshold value). In an alternative example, charging module 38 or other circuitry of IMD 14 may stop charging of the battery in response to determining that the slope of the current of the battery with time (i.e., di/dt) falls below a predetermined threshold, FIG. 9B includes graph 138B illustrating a theoretical charging routine or algorithm according to another example. As shown in the example of FIG. 9B, a constant current charging routine may be utilized in which IMD 14 controls charging current level 142B at a constant level. The charging voltage level 140B is a curve that represents the voltage changes over time until it eventually reaches a level (e.g., 4.5 volts) that is greater than the final charge voltage 144 of the battery (e.g., 3.0 volts). Again, because of the use of a lithium titanate material as the negative active material, lithium plating on the negative electrode may be avoided even though at some point during charging, the overpotential exceeds approximately 70 millivolts in one example. In this manner, charging of the battery may be accomplished at a relatively quick rate as compared to charging of batteries using conventional negative electrode materials (e.g., carbon, etc.). In one example, charging module 38 may control recharging of rechargeable power source 18 at the constant current of charging current level 142B.

To determine the point at which charging of the battery as shown in FIG. 9B should be terminated, various cutoff criteria may be utilized. For example, charging module 38 or other circuitry of IMD 14 may stop charging of the battery in response to IMD 14 determining that the voltage of the battery exceeds a predetermined threshold (i.e., the charging voltage level MOB rising above a predetermined threshold value, such as 4.5 volts). In another example, charging module 38 or other circuitry of IMD 14 may stop charging of the battery in response to determining that the slope of the voltage of the battery with time dV/dt) exceeds a predetermined threshold. In an alternative example, charging module 38 or other circuitry of IMD 14 may stop charging of the battery in response to determining that the slope of the voltage of the battery versus the capacity of the battery (i.e., dV/dQ) exceeds a predetermined threshold.

The charging voltages or current of FIGS. 9A and 9B may be selected by IMD 14 or charging device 20, for example, according to characteristics of rechargeable power source 18 or other characteristics of IMD 14. In one example, IMD 14 may also select a boost period of a higher power level for the constant voltage or constant current to achieve a voltage greater than the final voltage of rechargeable power source 18. IMD 14 may determine an estimated heat loss based on power initially delivered to rechargeable power source 18 when beginning the charging with the high power level (e.g., the voltage greater than the final voltage of the battery). IMD 14 may then select a boost period based on the estimated heat loss and continue to control charging module 38 to charge rechargeable power source 18 with the high power level for a duration of the selected boost period. Charging rates of 10 C or greater may be achieved during the selected boost period.

Figure 10:
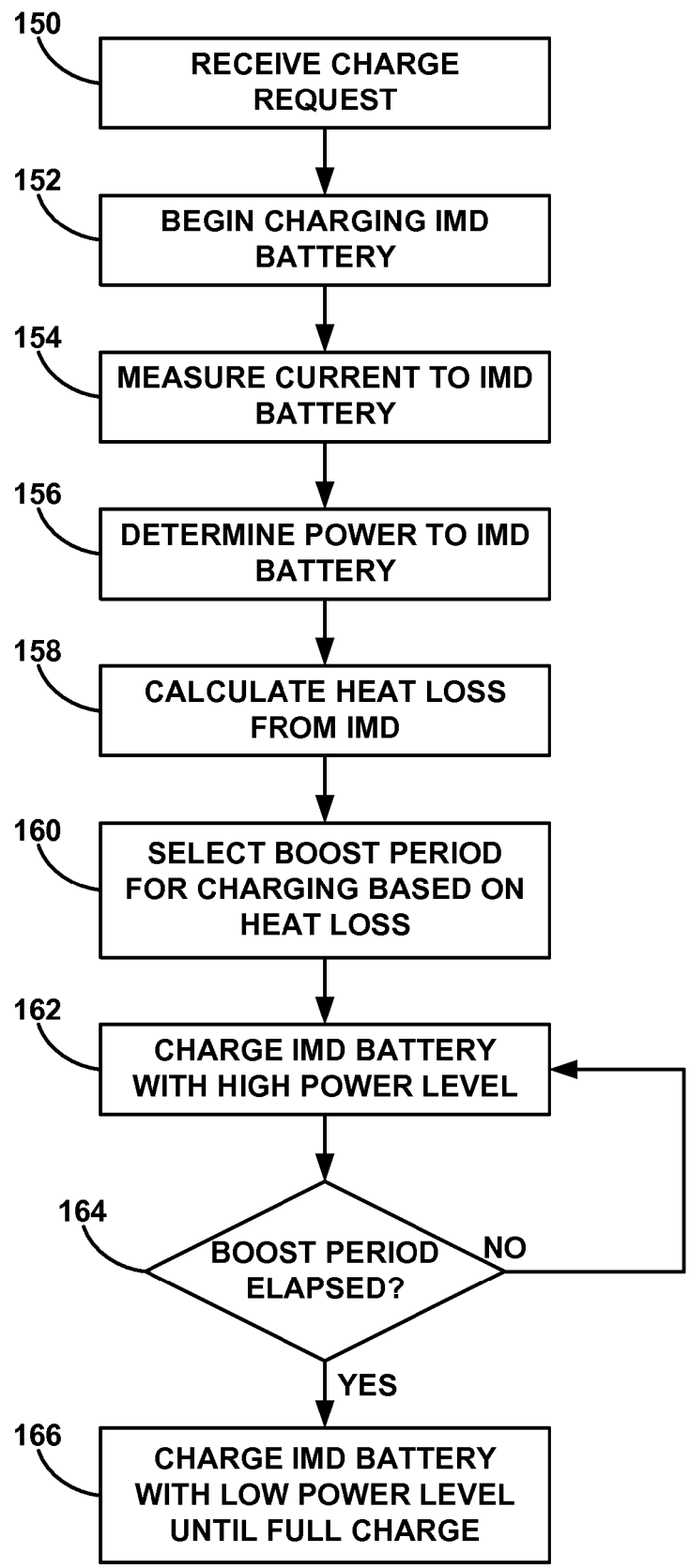
FIG. 10 is a flow diagram that illustrates an example technique for selecting a boost period based on estimated heat loss from the IMD.

FIG. 10 is a flow diagram that illustrates an example technique for selecting a boost period based on estimated heat loss from IMD 14. Although processor 50 of charging device 20 will be described as generally performing the technique of FIG. 10, the technique of FIG. 10 may instead be performed by a combination of processors 30 and 50, or other devices, in other examples.

A charging session for rechargeable power source 18 may begin when processor 50 receives a charge request via user interface 54 (150). In response, processor 50 may command charging module 58 to begin charging rechargeable power source 18 with a high power level (152). Upon beginning the charging session, charging module 38 or another circuit of IMD 14 may measure the electrical current delivered to rechargeable power source 18 of IMD 14 (154). Charging module 38 may also measure the voltage of rechargeable power source 18 so that processor 50 may multiply the measured voltage by the measured electrical current to rechargeable power source 18 to calculate the power delivered to rechargeable power source 18 (156). The measured current and voltage may be transmitted to charging device 20 by telemetry module 34 as charging data. In other examples, processor 30 may calculate the power delivered to rechargeable power source 18 and transmit the calculated power to charging device 20 as charging data.

Using the calculated power delivered to rechargeable power source 18, processor 50 may calculate the estimated heat loss from IMD 14 (158). As described herein, calculating the estimated heat loss may be performed using various techniques. For example, processor 50 may calculate the power delivered to primary coil 48 of charging device 20 and calculate the power lost in primary coil 48. Processor 50 may then subtract the power lost in primary coil 48 and the power delivered to rechargeable power source 18 from the power delivered to primary coil 48. These calculations may include measurements of electrical current and voltage between various components of the charging system, such as the current and/or voltage of primary coil 48 or between primary coil 48 and charging module 58.

Processor 50 may next select the boost period for charging based on the estimated heat loss (160). As described herein, the boost period may be selected from a lookup table, where a plurality of estimated heat loss values each correspond to respective boost periods. In other examples, processor 50 may calculate the boost period based on the estimated heat loss. Processor 50 may then control charging module 58 to use a high power level for charging rechargeable power source 18 during the boost period (162). The high power level may also be applied using a constant voltage or constant current as described in FIGS. 9A and 9B, respectively. If the boost period has not elapsed or expired ("NO" branch of block 164), charging module 58 may continue the charging session with the high power level (162).

If the boost period has elapsed ("YES" branch of block 164), processor 50 may control charging module 58 to charge rechargeable power source 18 with a low power level until rechargeable power source 18 is fully charged (166). As described herein, the low power level may provide a charge rate that does not provide enough heat to tissue surrounding IMD 14 sufficient to damage the tissue. In some examples, rechargeable power source 18 may be fully charged at the end of the boost period or even before the boost period expires. If rechargeable power source 18 becomes fully charged prior to the boost period expiring, processor 50 may terminate the charging session even if the boost period has not yet expired. In other examples, processor 50 may monitor the cumulative thermal dose to patient 12 after the boost period expires to select the appropriate power level and control the remainder of the charging session.

Figure 11:
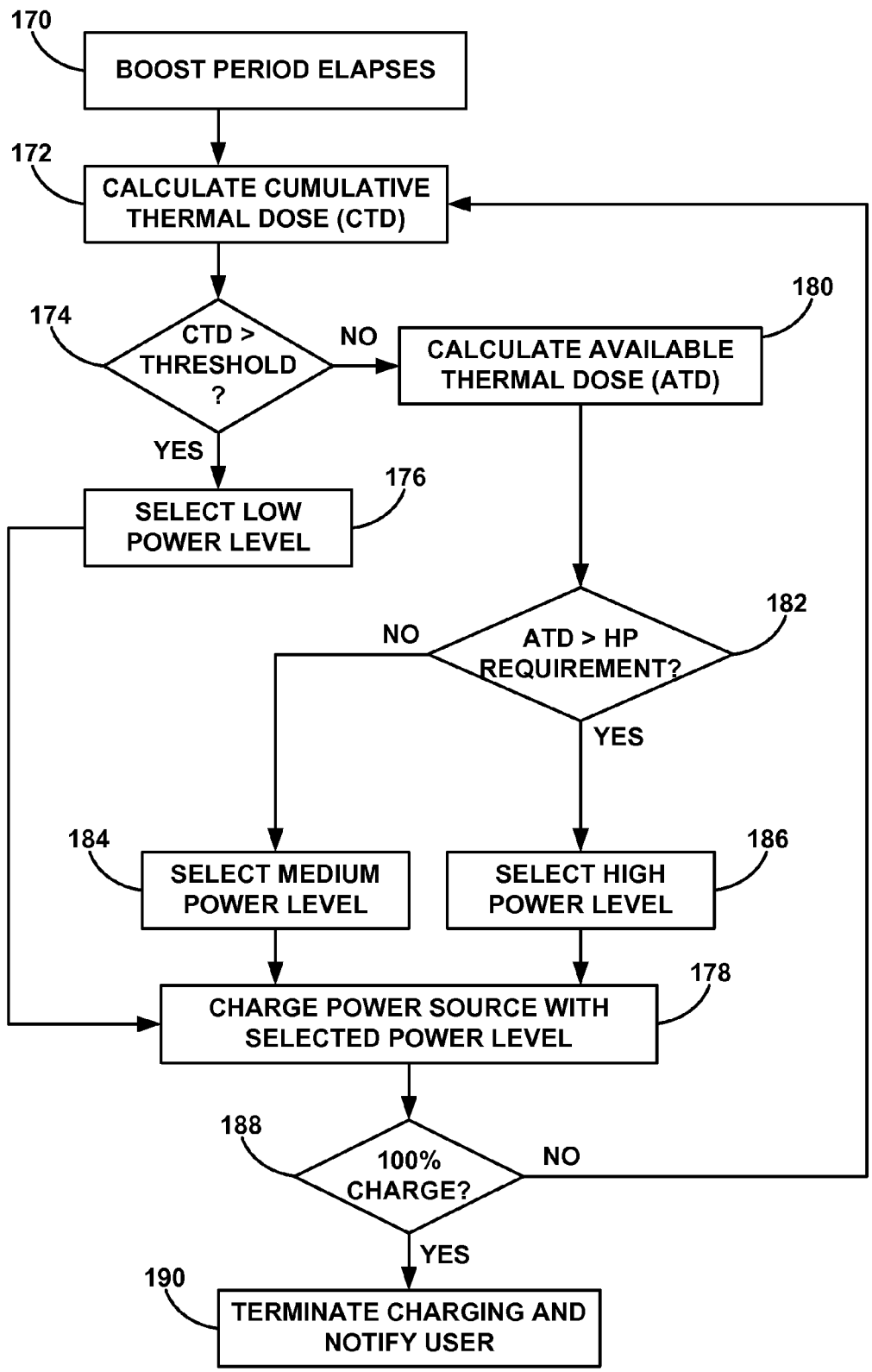
FIG. 11 is a flow diagram that illustrates an example technique for selecting a power level for charging an implantable rechargeable power source after a boost period expires based on an available cumulative thermal dose remaining for the charging process.

FIG. 11 is a flow diagram that illustrates an example technique for selecting a power level for charging rechargeable power source 18 after a boost period expires based on an available cumulative thermal dose remaining for the charging session. The available thermal dose after the boost period may allow charging power levels to be reduced prior to exceeding the thermal dose threshold. Although processor 50 of charging device 20 will be described as performing the technique of FIG. 11, the technique of FIG. 11 may instead be performed by processor 30 of IMD 14, or a combination of processors 30 and 50, in other examples.

After processor 50 terminates the boost period at the end of the boost period duration (170), processor 50 may calculate the cumulative thermal dose (CTD) to verify how much heat tissue surrounding IMD 14 has been exposed to recently (172). The cumulative thermal dose may include the dose delivered during the boost period and, in some examples, charging temperatures prior to the current charging session. If the cumulative thermal dose is less than the thermal dose threshold ("NO" branch of block 174), processor 50 calculates the available thermal dose (180). If the available thermal dose is greater than the high power dose requirement ("YES" branch of block 182), processor 50 selects the high power level for charging (186). As described herein, the high power dose requirement may be the available cumulative thermal dose for further high power level charging. If the available thermal dose is less than the high power dose requirement ("NO" branch of block 182), processor 50 selects the medium power level for charging (184). The medium power level may allow IMD 14 to lower its temperature, and lower the rate at which the cumulative thermal rate increases, while still charging rechargeable power source 18. In either the high power level or the medium power level case, rechargeable power source 18 may be charged using a constant voltage or constant current as described in FIGS. 9A and 9B, respectively.

If the cumulative thermal dose is equal to or greater than the thermal dose threshold ("YES" branch of block 174), processor 50 selects the low power level for charging (176). If processor 50 is switching to a different power level, user interface 54 may notify the user via a sound or visual indication that such change has occurred. After the selection of the appropriate power level, processor 50 then instructs charging module 58 to charge rechargeable power source 18 with the selected power level (178). This technique for selecting power levels for charging rechargeable power source 18 and IMD 14 may allow processor 50 to limit heat radiated by IMD 14 after the thermal dose threshold has been exceeded.

If rechargeable power source 18 has not yet reached a 100 percent, or full, charge level ("NO" branch of block 188), then processor 50 continues to calculate the cumulative thermal dose (172). If rechargeable power source 18 has reached a 100 percent, or full, charge level ("YES" branch of block 188), then processor 50 may instruct charging module 58 to terminate charging and notify the user of the termination (190). This notification may be in the form of an audible alert or visual indicator provided by user interface 54. Processor 50 may also terminate charging upon request from the user.

Figure 12:
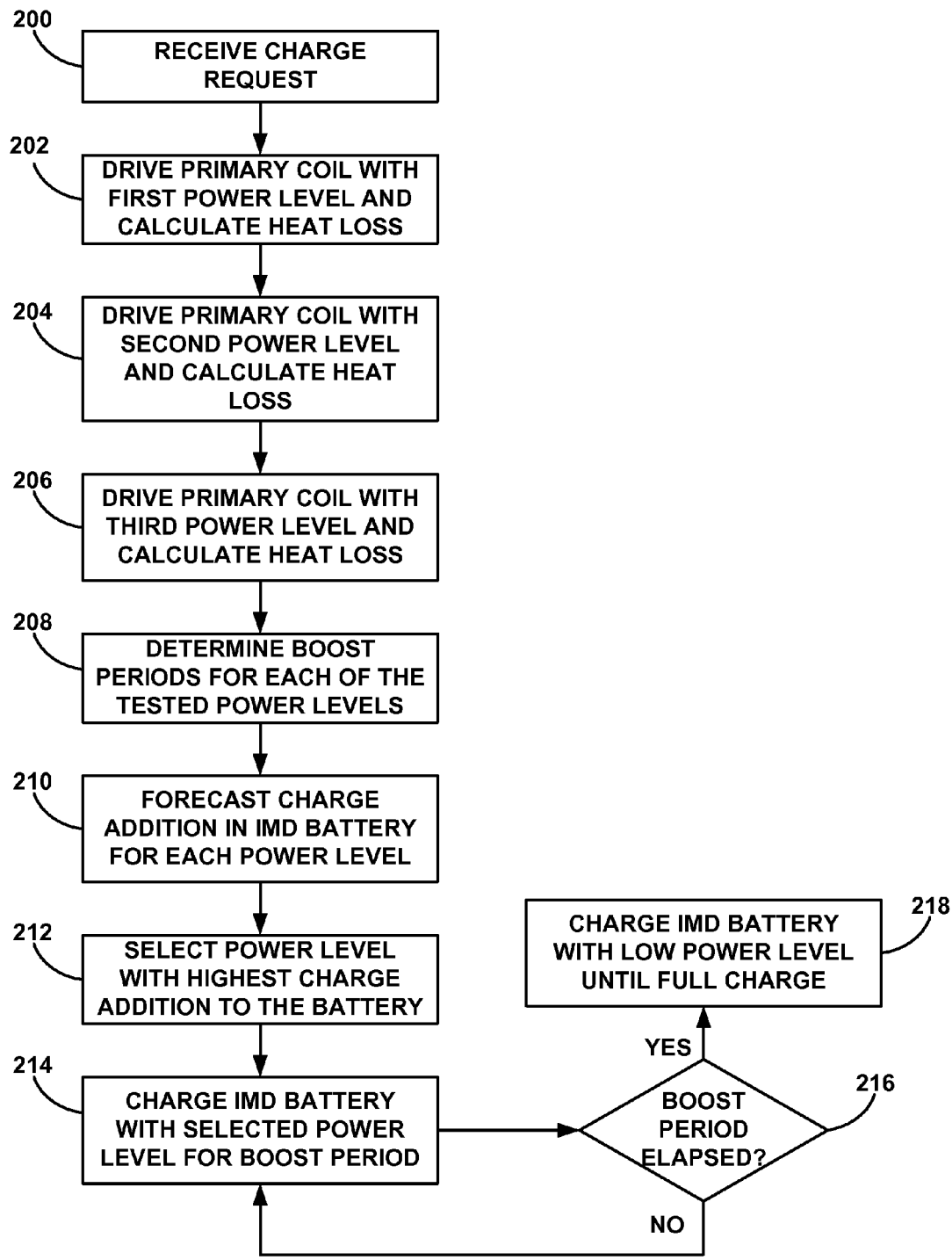
FIG. 12 is a flow diagram that illustrates an example technique for testing multiple power levels and selecting a power level that provides the highest charge level based on an estimated heat loss from the IMD.

FIG. 12 is a flow diagram that illustrates an example technique for testing multiple power levels and selecting a power level that provides the highest charge addition to the power source based on an estimated heat loss from IMD 14. Although processor 50 of charging device 20 will be described as generally performing the technique of FIG. 12, the technique of FIG. 12 may instead be performed by a combination of processors 30 and 50, or other devices, in other examples.

A charging session for rechargeable power source 18 may begin when processor 50 receives a charge request via user interface 54 (200). The charging session may begin with two or more test charges (although three test charges are disclosed in this example) that are used to evaluate the combination of power level and boost period that may result in the highest charge added to rechargeable power source 18 during a predetermined charging session. In other words, if patient 12 has a one hour session to charge rechargeable power source 18, the boost period does not need to be as short as possible with the highest possible power level. Instead, a longer boost period with a lower power level may result in a higher charge being added to rechargeable power source 18 over the charging session and still be within heat loss limits. Therefore processor 50 may select at least two different power levels to test and select the power level and respective boost period that may provide the highest added charge for the available time patient 12 has to charge rechargeable power source 18.

In the first test charge, processor 50 may command charging module 50 to drive primary coil 48 with a first power level and calculate the resulting heat loss (202). Processor 50 may calculate the resulting heat loss from the measured current to rechargeable power source 18 and determining the resulting power to rechargeable power source 18. Charging module 39 may measure the electrical current delivered to rechargeable power source 18 of IMD 14. Charging module 39, or another circuit, may also measuring the voltage of rechargeable power source 18 so that processor 50 may multiply the measured voltage by the measured electrical current to rechargeable power source 18 to calculate the power delivered to rechargeable power source 18. Telemetry module 34 may transmit the measured current and voltage to charging device 20 as charging data. In other examples, processor 30 may calculate the power delivered to rechargeable power source 18 and transmit the calculated power to charging device 20 as charging data. In addition, processor 50 may calculate the estimated heat loss from IMD 14 of the first power level using various techniques. For example, processor 50 may calculate the power delivered to primary coil 48 of charging device 20 and calculate the power lost in primary coil 48. Processor 50 may then subtract the power lost in primary coil 48 and the power delivered to rechargeable power source 18 from the power delivered to primary coil 48. These calculations may include measurements of electrical current and voltage between various components of the charging system, such as the current and/or voltage of primary coil 48 or between primary coil 48 and charging module 58. These processes for measuring current, determining power, and calculating the heat loss may be done for each of the following test charges of various power levels.

In the second test charge, processor 50 may command charging module 50 to drive primary coil 48 with a second power level and calculate the resulting heat loss (204). Next, for the third test charge, processor 50 may command charging module 50 to drive primary coil 48 with a third power level and calculate the resulting heat loss (206). The first, second, and third power levels are all different from each other. For example, the power levels may include a 2.0 watt (W) power level, a 1.5 W power level, and a 1.0 W power level. The magnitude of the power levels may be predetermined or selected based on criteria such as the available time for charging or the current charge level of rechargeable power source 18. In addition, the number of different power levels tested may be predetermined or selected based on one or more criteria such as the available time for charging.

After each of the test charges have been completed, processor 50 determines the boost periods for each of the tested power levels (208). As described herein, each boost period may be selected from a lookup table, where a plurality of estimated heat loss values each correspond to respective boost periods. Although boost periods for different power levels may be selected from the same lookup table, each power level may have a different lookup table with unique boost periods in other examples. In some examples, processor 50 may calculate each boost period using one or more equations based on the estimated heat loss. Instead of determining the boost periods after each of the test charges is completed, processor 50 may determine the boost period for each power level in response to calculating each respective heat loss (e.g., prior to conducting the subsequent test charge).

Processor 50 then forecasts, or calculates, the estimated charge addition to rechargeable power source 18 that would occur due to each power level and its selected boost period (210). This calculation may also include a low power (e.g., trickle) charge after the selected boost period for the remainder of the charging session. Processor 50 may calculate the charge addition by multiplying the electrical current of each power level delivered to rechargeable power source 18 by the boost period and the remainder of the charging session. For example, processor 50 may multiply 100 mA of current during a 2 W power level by 1/6 of an hour for a ten minute boost period and add the product of 50 mA of current during a trickle current and 5/6 of an hour for fifty minutes of the remainder of the charging session. The resulting charge addition may be approximately 58.3 milliamp hours (mAh). For comparison, a power level of 1.5 W may induce 75 mA of current during a half an hour boost period and the trickle charge of 50 mA may also occur for a half an hour. The result of this lower power level may be approximately 62.5 mAh. In these examples, the lower power level would provide a higher charge addition to rechargeable power source 18.

In response to calculating each charge addition, processor 50 selects the power level that would produces the highest charge addition to rechargeable power source 18 over the anticipated charging session (212). Using the selected power level and its respective boost period, processor 50 may then control charging module 58 to charge rechargeable power source 18 during the boost period (214). The selected power level may be applied to rechargeable power source 18 using a constant voltage or constant current as described in FIGS. 9A and 9B, respectively. If the boost period has not elapsed or expired ("NO" branch of block 216), charging module 58 may continue the charging session with the selected power level (214).

If the boost period has elapsed ("YES" branch of block 216), processor 50 may control charging module 58 to charge rechargeable power source 18 with the low power level (e.g., the trickle charge) until rechargeable power source 18 is fully charged or the charging session otherwise is terminated (218). As described herein, the low power level may provide a charge rate that does provide enough heat to tissue surrounding IMD 14 sufficient to damage the tissue. In some examples, rechargeable power source 18 may be fully charged at the end of the boost period or even before the boost period expires. If rechargeable power source 18 becomes fully charged prior to the boost period expiring, processor 50 may terminate the charging session even if the boost period has not yet expired. In other examples, processor 50 may monitor the cumulative thermal dose to patient 12 after the boost period expires to select the appropriate power level and control the remainder of the charging session.

According to the techniques and devices described herein, a boost period for charging a rechargeable power source of an IMD may be selected based on an estimated heat loss from the IMD. The estimated heat loss may be determined based on the power delivered to the rechargeable power source at the beginning of the charging session with the high power level. Heat loss may be a function of the coupling efficiency and the charging current induced in the IMD. Higher coupling efficiencies may lead to greater charging currents and/or longer boost periods. Lower coupling efficiencies may result in lower charging currents that generate lower heat within the secondary coil, but the charging signal will also be heating up materials of the IMD at the same time. In this manner, the boost period may be adaptive to the charging conditions specific to different patients and circumstances. After the boost period, the charging device may continue to charge the IMD at a low power level (e.g., a trickle charge). In other examples, the charging device may monitor the cumulative thermal dose after the boost period to ensure that tissue adjacent to the IMD is not damaged from high temperatures. Charging an IMD in this manner may allow the charging device to maximize the charging rate while reducing the potential for tissue damage. In other words, the adaptive boost period may balance fast charging rates with safety limits for the patient.

This disclosure is primary directed to wireless transfer of energy between two coils (e.g., inductive coupling). However, one or more aspects of this disclosure may also be applicable to energy transfer involving a physical connection between a charging device and a rechargeable power source. For example, aspects of this disclosure may be applicable to charging the power source of an IMD by inserting a needle coupled to an external charging device through the skin and into a port of the IMD. Although physical connections for energy transfer may not introduce heat losses due to energy transfer between wireless coils, heat may still be generated and lost to the patient from components within the IMD (e.g., the battery being charged and circuits involved in the recharging of the power source).

Various examples have been described. These and other examples are within the scope of the following claims.

What is claimed is:

1. A method comprising:
   controlling a charging module to begin charging a rechargeable power source of an implantable medical device with a high power level, wherein the high power level is higher than a non-zero low power level;
   determining, by a processor, an estimated heat loss based on power initially delivered to the rechargeable power source when beginning the charging with the high power level;
   selecting, by the processor, a boost period based on the estimated heat loss; and
   continuing to control the charging module to charge the rechargeable power source with the high power level for a duration of the boost period.

2. The method of claim 1, further comprising:
   comparing a high power charging time to the boost period, wherein the high power charging time is an elapsed time with which the rechargeable power source was charged with the high power level; and
   terminating charging with the high power level when the high power charging time exceeds the duration of the boost period.

3. The method of claim 2, further comprising:
   selecting the low power level when the high power charging time exceeds the boost period; and
   charging the rechargeable power source with the low power level until the rechargeable power source is fully charged, wherein the low power level comprises a lower power level than the high power level.

4. The method of claim 1, wherein determining the estimated heat loss comprises:
   calculating a power delivered to a primary coil of an external charging device;
   calculating a power lost in the primary coil; and
   subtracting the power lost in the primary coil and the power delivered to the rechargeable power source from the power delivered to the primary coil.

5. The method of claim 1, further comprising calculating the power delivered to the rechargeable power source by measuring an electrical current flowing to the rechargeable power source, measuring a voltage of the rechargeable power source, and multiplying the electrical current by the voltage.

6. The method of claim 1, wherein:
   selecting the boost period comprises selecting one of a plurality of boost periods that corresponds to the estimated heat loss; and
   the plurality of boost periods comprise different durations of time.

7. The method of claim 1, wherein the duration of the boost period is between approximately 5 minutes and 35 minutes.

8. The method of claim 1, further comprising:
   generating a first electrical current in a primary coil of a charging device based on the high power level; and
   inducing an electrical current in an implanted secondary coil to charge the rechargeable power source.

9. The method of claim 1, further comprising:
calculating, by the processor, an estimated cumulative thermal dose delivered to the patient during charging of the rechargeable power source over at least the duration of the boost period; and
selecting, by the processor, a subsequent power level for charging the rechargeable power source after the boost period based on the estimated cumulative thermal dose.

10. The method of claim 1, wherein the processor is housed by one of the implantable medical device or an external charging device.

11. The method of claim 1, wherein the high power level is a first power level, and wherein the method further comprises:
controlling the charging module to begin charging the rechargeable power source of an implantable medical device with a second power level different than the first power level;
determining, by the processor, an estimated heat loss for the second power level based on power delivered to the rechargeable power source when charging with the second power level;
selecting, by the processor, a boost period based on the estimated heat loss for the second power level;
calculating a first charge addition to the rechargeable power source for the first power level during the boost period of the first power level;
calculating a second charge addition to the rechargeable power source for the second power level during the boost period of the second power level;
determining a highest charge addition by comparing the first forecast charge addition to the second forecast charge addition; and
selecting, by the processor, the first power level for charging the rechargeable power source when the first power level is associated with the highest charge addition.

12. The method of claim 1, wherein the rechargeable power source comprises a negative electrode comprising lithium titanate.

13. The method of claim 1, wherein continuing to control the charging module to charge the rechargeable power source with the high power level comprises controlling the charging module to charge the rechargeable power source at a charge rate greater than approximately 0.5 C.

14. The method of claim 1, wherein continuing to control the charging module to charge the rechargeable power source with the high power level comprises controlling the charging module to charge the rechargeable power source at a charge rate greater than approximately 5.0 C.

15. The method of claim 1, wherein continuing to control the charging module to charge the rechargeable power source with the high power level comprises controlling the charging module to charge the rechargeable power source at a constant voltage greater than a full charge voltage of the rechargeable power source.

16. A system comprising:
a processor configured to:
control a charging module to begin charging a rechargeable power source of an implantable medical device with a high power level, wherein the high power level is higher than a non-zero low power level;
determine an estimated heat loss based on power initially delivered to the rechargeable power source when beginning to charge the rechargeable power source with the high power level;
select a boost period based on the estimated heat loss; and
continue to control the charging module to charge the rechargeable power source with the high power level for a duration of the boost period.

17. The system of claim 16, wherein the processor is configured to:
compare a high power charging time to the boost period, wherein the high power charging time is an elapsed time with which the rechargeable power source was charged with the high power level; and
terminate charging with the high power level when the high power charging time exceeds the duration of the boost period.

18. The system of claim 17, further comprising a charging module, wherein:
the processor is configured to select the low power level when the high power charging time exceeds the boost period;
the charging module is configured to charge the rechargeable power source with the low power level until the rechargeable power source is fully charged; and
the low power level comprises a lower power level than the high power level.

19. The system of claim 16, wherein the processor is configured to:
calculate a power delivered to a primary coil of an external charging device;
calculate a power lost in the primary coil; and
subtract the power lost in the primary coil and the power delivered to the rechargeable power source from the power delivered to the primary coil to determine the estimated heat loss.

20. The system of claim 19, wherein the processor is configured to multiply a measured electrical current flowing to the rechargeable power source by a measured voltage of the rechargeable power source to calculate the power delivered to the rechargeable power source.

21. The system of claim 16, further comprising a memory configured to store a plurality of boost periods each comprising different durations of time, wherein the processor is configured to select one of the plurality of boost periods that corresponds to the estimated heat loss.

22. The system of claim 16, wherein the duration of the boost period is between approximately 5 minutes and 35 minutes.

23. The system of claim 16, further comprising:
an external charging device configured to generate a first electrical current in a primary coil of the charging device based on the high power level;
a secondary coil configured to be implanted in a patient and produce a second electrical current induced by a magnetic field of the primary coil, wherein the secondary coil is associated with the rechargeable power source; and
a telemetry module configured to receive charging data from the implantable medical device, wherein the charging data comprises a measured electrical current flowing to the rechargeable power source and a measured voltage of the rechargeable power source.

24. The system of claim 16, wherein the processor is configured to:
calculate an estimated cumulative thermal dose delivered to the patient during charging of the rechargeable power source over at least the duration of the boost period; and
select a subsequent power level for charging the rechargeable power source after the boost period based on the estimated cumulative thermal dose.

25. The system of claim 16, wherein the processor is contained within one of the implantable medical device or a charging device configured to charge the rechargeable power source.

26. The system of claim 16, further comprising the rechargeable power source, wherein the rechargeable power source comprises a negative electrode comprising lithium titanate.

27. The system of claim 16, wherein the processor is configured to control the charging module to charge the rechargeable power source at a charge rate greater than approximately 0.5 C.

28. The system of claim 16, wherein the processor is configured to control the charging module to charge the rechargeable power source at a charge rate greater than approximately 5.0 C.

29. The system of claim 16, further comprising a charging module of the implantable medical device, wherein the charging module is configured to charge the rechargeable power source at a constant voltage greater than a full charge voltage of the rechargeable power source.

30. A computer-readable storage medium comprising instructions that cause at least one processor to:
control a charging module to begin charging a rechargeable power source of an implantable medical device with a high power level, wherein the high power level is higher than a non-zero low power level;
determine an estimated heat loss based on power initially delivered to the rechargeable power source when beginning the charging with the high power level;
select a boost period based on the estimated heat loss; and
continue to control the charging module to charge the rechargeable power source with the high power level for a duration of the boost period.

31. The computer-readable storage medium of claim 30, further comprising instructions that cause the at least one processor to:
compare a high power charging time to the boost period, wherein the high power charging time is an elapsed time with which the rechargeable power source was charged with the high power level; and
terminate charging with the high power level when the high power charging time exceeds the boost period.

32. The computer-readable storage medium of claim 31, further comprising instructions that cause the at least one processor to calculate the power delivered to the rechargeable power source by measuring an electrical current flowing to the rechargeable power source, measuring a voltage of the rechargeable power source, and multiplying the electrical current by the voltage, wherein the instructions that cause the at least one processor to determine the estimated heat loss comprise instructions that cause the at least one processor to:
calculate a power delivered to a primary coil of an external charging device;
calculate a power lost in the primary coil; and
subtract the power lost in the primary coil and the power delivered to the rechargeable power source from the power delivered to the primary coil.

33. A system comprising:
means for controlling a charging module to begin charging a rechargeable power source of an implantable medical device with a high power level, wherein the high power level is higher than a non-zero low power level;
means for determining an estimated heat loss based on power initially delivered to the rechargeable power source when beginning the charging with the high power level; and
means for selecting a boost period based on the estimated heat loss, wherein the means for controlling the charging module to begin charging the rechargeable power source comprises means for continuing to control the charging module to charge the rechargeable power source with the high power level for a duration of the boost period.

* * * * *